(12) United States Patent
Wang et al.

(10) Patent No.: US 7,452,996 B2
(45) Date of Patent: Nov. 18, 2008

(54) SUBSTITUTED QUINOLINE DERIVATIVES

(75) Inventors: Weibo Wang, Moraga, CA (US); Ryan N. Constantine, Salt Lake City, UT (US); Liana Marie Lagniton, Berkeley, CA (US); Kenneth Bair, Emeryville, CA (US)

(73) Assignee: Novartis Vaccines and Diagnostics, Inc., Emmeryville, CA (US)

( * ) Notice: Subject to any disclaimer, the term of this patent is extended or adjusted under 35 U.S.C. 154(b) by 611 days.

(21) Appl. No.: 11/133,509

(22) Filed: May 19, 2005

(65) Prior Publication Data
US 2005/0261337 A1 Nov. 24, 2005

Related U.S. Application Data

(60) Provisional application No. 60/573,120, filed on May 21, 2004.

(51) Int. Cl.
*C07D 271/00* (2006.01)
(52) U.S. Cl. ................................ 546/159; 546/153
(58) Field of Classification Search ............... 546/153, 546/159
See application file for complete search history.

(56) References Cited

U.S. PATENT DOCUMENTS

| | | | |
|---|---|---|---|
| 6,172,087 B1 * | 1/2001 | Steiner et al. | 514/339 |
| 6,545,004 B1 | 4/2003 | Finer et al. | |
| 6,562,831 B1 | 5/2003 | Finer et al. | |
| 6,630,479 B1 | 10/2003 | Finer et al. | |

FOREIGN PATENT DOCUMENTS

| WO | WO 00/59887 | | 10/2000 |
|---|---|---|---|
| WO | WO 01/30768 | A1 | 5/2001 |
| WO | WO 01/98278 | A1 | 12/2001 |
| WO | WO 02/28839 | A1 | 4/2002 |
| WO | WO 02/056880 | A1 | 7/2002 |
| WO | WO 02/057244 | A1 | 7/2002 |
| WO | WO 02/083143 | A1 | 10/2002 |
| WO | WO 03/039460 | A2 | 5/2003 |
| WO | WO 03/043995 | A1 | 5/2003 |
| WO | WO 03/049527 | A2 | 6/2003 |
| WO | WO 03/049678 | A2 | 6/2003 |
| WO | WO 03/049679 | A2 | 6/2003 |
| WO | WO 03/050064 | A2 | 6/2003 |
| WO | WO 03/050122 | A2 | 6/2003 |
| WO | WO 03/059289 | A2 | 7/2003 |
| WO | WO 03/070701 | A2 | 8/2003 |
| WO | WO 03/079973 | A2 | 10/2003 |
| WO | WO 03/088903 | A2 | 10/2003 |
| WO | WO 03/094839 | A2 | 11/2003 |
| WO | WO 03/097053 | A1 | 11/2003 |
| WO | WO 03/099211 | A2 | 12/2003 |
| WO | WO 03/103575 | A2 | 12/2003 |
| WO | WO 03/105855 | A1 | 12/2003 |
| WO | WO 03/106417 | A1 | 12/2003 |
| WO | WO 03/106426 | A1 | 12/2003 |
| WO | WO 2004/004652 | A2 | 1/2004 |
| WO | WO 2004/006865 | A2 | 1/2004 |
| WO | WO 2004/009036 | A2 | 1/2004 |
| WO | WO 2004/018058 | A2 | 3/2004 |
| WO | WO 2004/024086 | A2 | 3/2004 |
| WO | WO 2004/026226 | A1 | 4/2004 |

* cited by examiner

*Primary Examiner*—D. Margaret Seaman
(74) *Attorney, Agent, or Firm*—Vinit Kathardekar; Lorna Tanner

(57) ABSTRACT

The present invention relates to new substituted quinoline compounds and pharmaceutically acceptable salts, esters or prodrugs thereof, compositions of the new compounds together with pharmaceutically acceptable carriers, and uses of the new compounds. The compounds of the invention have the following general formula:

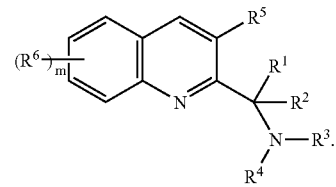

33 Claims, No Drawings

SUBSTITUTED QUINOLINE DERIVATIVES

This application claims the benefit under 35 U.S.C. §119 (e) of U.S. Provisional Application Ser. No. 60/573,120, filed May 21, 2004, which is hereby incorporated by reference in its entirety.

BACKGROUND OF THE INVENTION

1. Field of the Invention

The present invention relates to substituted quinoline compounds and pharmaceutically acceptable salts, esters or prodrugs thereof, compositions of these compounds together with pharmaceutically acceptable carriers, and uses of these compounds.

2. State of the Art

Kinesins are motor proteins that use adenosine triphosphate to bind to microtubules and generate mechanical force. Kinesins are characterized by a motor domain having about 350 amino acid residues. The crystal structures of several kinesin motor domains have been resolved.

Currently, about one hundred kinesin-related proteins (KRP) have been identified. Kinesins are involved in a variety of cell biological processes including transport of organelles and vesicles, and maintenance of the endoplasmic reticulum. Several KRPs interact with the microtubules of the mitotic spindle or with the chromosomes directly and appear to play a pivotal role during the mitotic stages of the cell cycle. These mitotic KRPs are of particular interest for the development of cancer therapeutics.

Kinesin spindle protein (KSP) (also known as EgS, HsEg5, KNSL1, or KIFII) is one of several kinesin-like motor proteins that are localized to the mitotic spindle and known to be required for formation and/or function of the bipolar mitotic spindle.

In 1995, the depletion of KSP using an antibody directed against the C-terminus of KSP was shown to arrest HeLa cells in mitosis with monoastral microtubule arrays (Blangy et al., *Cell* 83:1159-1169, 1995). Mutations in bimC and cut7 genes, which are considered to be homologues of KSP, cause failure in centrosome separation in *Aspergillus nidulans* (Enos, A. P., and N. R. Morris, *Cell* 60:1019-1027, 1990) and *Schizosaccharomyces pombe* (Hagan, I., and M. Yanagida, *Nature* 347:563-566, 1990). Treatment of cells with either ATRA (all trans-retinoic acid), which reduces KSP expression on the protein level, or depletion of KSP using antisense oligonucleotides revealed a significant growth inhibition in DAN-G pancreatic carcinoma cells indicating that KSP might be involved in the antiproliferative action of all trans-retinoic acid (Kaiser, A., et al., *J. Biol. Chem.* 274, 18925-18931, 1999). Interestingly, the *Xenopus laevis* Aurora-related protein kinase pEg2 was shown to associate and phosphorylate XlEg5 (Giet, R., et al., *J. Biol. Chem.* 274:15005-15013, 1999). Potential substrates of Aurora-related kinases are of particular interest for cancer drug development. For example, Aurora 1 and 2 kinases are overexpressed on the protein and RNA level and the genes are amplified in colon cancer patients.

The first cell permeable small molecule inhibitor for KSP, "monastrol," was shown to arrest cells with monopolar spindles without affecting microtubule polymerization as do conventional chemotherapeutics such as taxanes and vinca alkaloids (Mayer, T. U., et al., *Science* 286:971-974, 1999). Monastrol was identified as an inhibitor in phenotype-based screens and it was suggested that this compound may serve as a lead for the development of anticancer drugs. The inhibition was determined not to be competitive in respect to adenosine triphosphate and to be rapidly reversible (DeBonis, S., et al., *Biochemistry* 42:338-349, 2003; Kapoor, T. M., et al., *J. Cell Biol.* 150:975-988, 2000).

In light of the importance of improved chemotherapeutics, there is a need for KSP inhibitors that are effective in vivo inhibitors of KSP and KSP-related proteins.

SUMMARY OF THE INVENTION

Compounds of the Invention

This invention is directed to substituted quinoline compounds represented by the formula I:

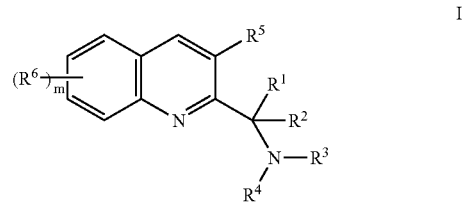

wherein:

m is an integer from 0 to 3;

$R^1$ is selected from the group consisting of acylamino, carboxyl ester, and $C_1$ to $C_5$ alkyl optionally substituted with hydroxy, or halo;

$R^2$ is hydrogen or $C_1$ to $C_5$ alkyl;

$R^3$ is —C(=X)-A, wherein A is selected from the group consisting of aryl, heteroaryl, heterocyclic, and cycloalkyl, all of which may be optionally substituted with 1 to 4 substituents selected from the group consisting of $C_1$ to $C_4$ alkyl, $C_1$ to $C_4$ alkoxy, halo, hydroxy, and nitro and X is oxygen or sulfur;

$R^4$ is -alkylene-heterocyclic or -alkylene-$NR^7R^8$ wherein alkylene is a $C_1$ to $C_4$ straight chained alkylene; $R^7$ and $R^8$ are independently selected from the group consisting of hydrogen, $C_1$ to $C_4$ alkyl, arylalkyl, heteroarylalkyl, cycloalkyl and cycloalkylalkyl;

$R^5$ is selected from the group consisting of L-$A^1$, wherein $A^1$ is selected from the group consisting of aryl, heteroaryl, heterocyclic, and cycloalkyl, all of which may be optionally substituted with 1 to 4 substituents selected from the group consisting of $C_1$ to $C_4$ alkyl, $C_1$ to $C_4$ alkoxy, halo, hydroxy, and nitro and wherein L is selected from the group consisting of oxygen, —$NR^9$ where $R^9$ is hydrogen or alkyl, —S(O)$_q$— where q is zero, one or two, and $C_1$ to $C_5$ alkylene, optionally substituted with hydroxy, halo, or acylamino; and $R^6$ is selected from the group consisting of $C_1$ to $C_5$ alkyl, $C_2$ to $C_5$ alkenyl, $C_2$ to $C_5$ alkynyl, —$CF_3$, $C_1$ to $C_5$ alkoxy, halo, and hydroxy;

or pharmaceutically acceptable salts, esters or prodrugs thereof.

In another preferred embodiment, the compounds of this invention are represented by formula II:

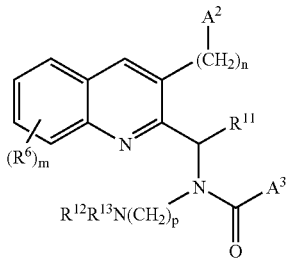

wherein:
A² and A³ are independently selected from the group consisting of aryl, heteroaryl, heterocyclic, and cycloalkyl, all of which may be optionally substituted with 1 to 4 substituents selected from the group consisting of $C_1$ to $C_4$ alkyl, $C_1$ to $C_4$ alkoxy, halo, hydroxy, and nitro;

each $R^6$ is independently selected from the group consisting of $C_1$ to $C_5$ alkyl, $C_2$ to $C_5$ alkenyl, $C_2$ to $C_5$ alkynyl, —$CF_3$, $C_1$ to $C_5$ alkoxy, halo and hydroxyl;

$R^{11}$ is $C_2$ to $C_3$ alkyl;

$R^{12}$ and $R^{13}$ are independently selected from the group consisting of hydrogen, $C_1$ to $C_4$ alkyl, arylalkyl, heteroarylalkyl, cycloalkyl and cycloalkylalkyl;

m is an integer equal to 0 to 3;

n is an integer equal to 1 to 3; and p is an integer equal to 1 to 4;

or pharmaceutically acceptable salts, esters and prodrugs thereof.

In still a further preferred embodiment, the compounds of this invention are represented by formula III:

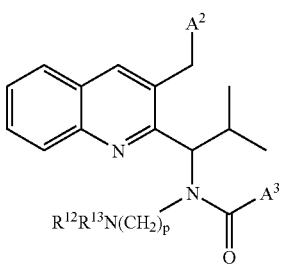

wherein:
A² and A³ are independently selected from the group consisting of aryl, heteroaryl, heterocyclic, and cycloalkyl, all of which may be optionally substituted with 1 to 4 substituents selected from the group consisting of $C_1$ to $C_4$ alkyl, $C_1$ to $C_4$ alkoxy, halo, hydroxy, and nitro;

$R^{12}$ and $R^{13}$ are independently selected from the group consisting of hydrogen, $C_1$ to $C_4$ alkyl, arylalkyl, heteroarylalkyl, cycloalkyl and cycloalkylalkyl;

p is an integer equal to 1 to 4;

or pharmaceutically acceptable salts, esters and prodrugs thereof.

PREFERRED EMBODIMENTS

In compounds of formula I, preferably, $R^1$ is $C_1$ to $C_5$ alkyl and more preferably $R^1$ is isopropyl or t-butyl.

In compounds of formula I, preferably $R^2$ is hydrogen or methyl.

In compounds of formula I, preferably X is oxygen. In compounds of formulae I, II and III, preferably A is aryl and more preferably A is phenyl or naphthyl. In other compounds of formulae I, II and III, preferably A is heteroaryl and more preferably A is selected from the group consisting of pyridinyl, imidazolyl, furanyl, pyrazolyl, and thiazolyl. In still other compounds of formulae I, II and III, preferably A is cycloalkyl and more preferably A is cyclohexyl.

Preferably, A is substituted with 1 to 4 substituents selected from the group consisting of chloro, methyl, bromo, fluoro, nitro, —$CF_3$, methoxy, and t-butyl.

Still more preferably, —C(O)-A is selected from the group consisting of:
(2-chloro-6-methylpyridin-4-yl)carbonyl;
(5-methylimidazol-4-yl)carbonyl;
(naphth-2-yl)carbonyl;
(pyridin-3-yl)carbonyl;
(pyridin-4-yl) carbonyl;
3,4-difluorobenzoyl;
3,4-dimethylbenzoyl;
3,5-dimethylpyrazol-3-ylcarbonyl;
2-(3-aminopropanamido)-4-methylbenzoyl;
2,4-difluorobenzoyl;
2,6-difluorobenzoyl;
2-chlorobenzoyl;
2-chloropyridin-3-ylcarbonyl;
2-chloropyridin-5-ylcarbonyl;
2-fluorobenzoyl;
2-methoxybenzoyl;
3,4-dichlorobenzoyl;
3-chlorobenzoyl;
3-fluoro-4-methylbenzoyl;
4-bromobenzoyl;
4-chlorobenzoyl;
4-hydroxybenzoyl;
4-methoxybenzoyl;
4-methyl-3-fluorobenzoyl;
4-methylbenzoyl;
4-nitrobenzoyl;
4-t-butylbenzoyl;
4-trifluoromethylbenzoyl;
benzoyl;
cyclohexylcarbonyl;
furan-3-ylcarbonyl;
pyridin-2-ylcarbonyl; and
thiazol-4-ylcarbonyl.

Most preferably, —C(O)-A is selected from the group consisting of 4-methyl-3-fluorobenzoyl, 4-methylbenzoyl, and 3,4-dimethylbenzoyl.

In one embodiment, $A^3$ is selected from the group consisting of 4-methyl-3-fluorophenyl, 4-methylphenyl, and 3,4-dimethylphenyl.

In a preferred embodiment $R^4$ is selected from the group consisting of:
3-(benzylamino) propyl;
3-(cyclobutylamino) propyl;
3-(cyclohexylmethylamino) propyl;
3-(diethylamino)propyl;
3-(isopropylamino) propyl;
3-[(3-trifluoromethylpyridin-6-yl)amino]propyl;
3-aminopropyl;

2-aminoethyl;
piperidin-3-ylmethyl; and
pyrrolidin-3-ylmethyl.

In other embodiments, $R^4$ is 3-aminopropyl.

In some embodiments, $R^5$ is alkylene-$A^1$ and $A^1$ is aryl. In still other embodiments, $R^5$ is benzyl.

Preferably, $R^5$ is selected from the group consisting of:
benzyl;
2-methylbenzyl;
3,5-difluorobenzyl;
3-acetylaminobenzyl;
3-fluorobenzyl;
3-hydroxybenzyl;
4-chlorobenzyl;
4-difluorobenzyl; and
4-methylbenzyl.

In compounds of formulae I, II and III, preferably $R^6$ is selected from the group consisting of:
hydrogen;
fluoro;
chloro;
methyl;
bromo;
ethyl;
vinyl;
methoxy;
phenyl;
ethynyl; and
—$CF_3$.

In compounds of formula II, preferred embodiments include m is 1, n is 1, $R^{11}$ is isopropyl, p is 3, $R^{12}$ and $R^{13}$ are hydrogen, $A^2$ is phenyl and $A^3$ aryl substituted with $C_1$ to $C_4$ alkyl, and/or halo.

In compounds of formula III, preferred embodiments include $A^2$ is phenyl, $A^3$ aryl substituted with $C_1$ to $C_4$ alkyl, and/or halo, p is 3 and $R^{12}$ and $R^{13}$ are hydrogen.

Substituted quinoline derivatives within the scope of this invention are exemplified by those set forth in Table 1 as follows.

TABLE 1

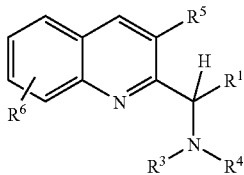

| Cmpd No. | $R^1$ | $R^3$ | $R^4$ | $R^5$ | $R^6$ |
|---|---|---|---|---|---|
| 1 | iso-propyl | 4-methyl-1-fluoro-benzoyl | 3-amino-propyl | benzyl | H |
| 2 | iso-propyl | 4-methylbenzoyl | 3-amino-propyl | benzyl | H |
| 3 | iso-propyl | 3,4-dimethylbenzoyl | 3-amino-propyl | benzyl | H |
| 4 | iso-propyl | 4-methylbenzoyl | 3-amino-propyl | benzyl | 7-chloro |
| 5 | iso-propyl | 4-methyl-3-fluoro-benzoyl | 3-amino-propyl | benzyl | 7-chloro |

Specific compounds within the scope of this invention are exemplified by the following:

N-(3-aminopropyl)-N-[1-(3-benzylquinolin-2-yl)-2-methylpropyl]-3-fluoro-4-methylbenzamide;

N-(3-aminopropyl)-N-[1-(3-benzylquinolin-2-yl)-2-methylpropyl]-4-methylbenzamide;

N-(3-aminopropyl)-N-[1-(3-benzylquinolin-2-yl)-2-methylpropyl]-3,4-dimethylbenzamide;

N-(3-aminopropyl)-N-[1-(3-benzyl-7-chloroquinolin-2-yl)-2-methylpropyl]-4-methylbenzamide;

N-(3-aminopropyl)-N-[1-(3-benzyl-7-chloroquinolin-2-yl)-2-methylpropyl]-3-fluoro-4-methylbenzamide; and pharmaceutically acceptable salts, esters and prodrugs thereof.

Methods and Compositions of the Invention

Also provided is a composition comprising a compound of formulae I, II and/or III (including mixtures thereof) and a pharmaceutically acceptable excipient or carrier.

In another aspect, the present invention provides methods of treating a mammalian patient suffering from a disorder mediated, at least in part by KSP. Thus, the present invention provides methods of treating a mammalian patient in need of such treatment comprising administering to the patient a therapeutically effective amount of a compound of formulae I, II, and/or III (including mixtures thereof) either alone or in combination with other anticancer agents.

DETAILED DESCRIPTION OF THE INVENTION

Definitions

As discussed above, the present invention is directed to new substituted quinoline compounds.

It is to be understood that the terminology used herein is for the purpose of describing particular embodiments only and is not intended to limit the scope of the present invention. It must be noted that as used herein and in the claims, the singular forms "a," "and" and "the" include plural referents unless the context clearly dictates otherwise. In this specification and in the claims which follow, reference will be made to a number of terms which shall be defined to have the following meanings:

Unless otherwise defined herein, "alkyl" refers to monovalent saturated aliphatic hydrocarbyl groups having from 1 to 5 carbon atoms and more preferably 1 to 3 carbon atoms. This term is exemplified by groups such as methyl, ethyl, n-propyl, iso-propyl, n-butyl, t-butyl, n-pentyl and the like.

"Substituted alkyl" refers to an alkyl group having from 1 to 3, and preferably 1 to 2, substituents selected from the group consisting of alkoxy, substituted alkoxy, acyl, acylamino, acyloxy, amino, substituted amino, aminoacyl, aryl, substituted aryl, aryloxy, substituted aryloxy, cyano, halogen, hydroxyl, nitro, carboxyl, carboxyl esters, cycloalkyl, substituted cycloalkyl, spirocycloalkyl, heteroaryl, substituted heteroaryl, heterocyclic, and substituted heterocyclic.

"Alkylene" refers to divalent saturated aliphatic hydrocarbyl groups preferably having from 1 to 5 and more preferably 1 to 3 carbon atoms which are either straight-chained or branched. This term is exemplified by groups such as methylene (—$CH_2$—), ethylene (—$CH_2CH_2$—), n-propylene (—$CH_2CH_2CH_2$—), iso-propylene (—$CH_2CH(CH_3)$—) and the like.

Unless otherwise defined herein, "alkoxy" refers to the group "alkyl-O-" which includes, by way of example, methoxy, ethoxy, n-propoxy, iso-propoxy, n-butoxy, t-butoxy, sec-butoxy, n-pentoxy and the like.

"Substituted alkoxy" refers to the group "substituted alkyl-O-".

"Acyl" refers to the groups H—C(O)—, alkyl-C(O)—, substituted alkyl-C(O)—, alkenyl-C(O)—, substituted alkenyl-C(O)—, alkynyl-C(O)—, substituted alkynyl-C(O)-cycloalkyl-C(O)—, substituted cycloalkyl-C(O)—, aryl-C(O)—, substituted aryl-C(O)—, heteroaryl-C(O)—, substituted heteroaryl-C(O)—, heterocyclic-C(O)—, and substituted heterocyclic-C(O)—, wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Aminoacyl" refers to the group —C(O)NR$^{10}$R$^{10}$ where each R$^{10}$ is independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, heteroaryl, substituted heteroaryl, heterocyclic, substituted heterocyclic and where each R$^{10}$ is joined to form together with the nitrogen atom a heterocyclic or substituted heterocyclic ring wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Acyloxy" refers to the groups alkyl-C(O)O—, substituted alkyl-C(O)O—, alkenyl-C(O)O—, substituted alkenyl-C(O)O—, alkynyl-C(O)O—, substituted alkynyl-C(O)O—, aryl-C(O)O—, substituted aryl-C(O)O—, cycloalkyl-C(O)O—, substituted cycloalkyl-C(O)O—, heteroaryl-C(O)O—, substituted heteroaryl-C(O)O—, heterocyclic-C(O)O—, and substituted heterocyclic-C(O)O— wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Alkenyl" refers to alkenyl groups having from 2 to 6 carbon atoms and preferably 2 to 4 carbon atoms and having at least 1 and preferably from 1 to 2 sites of alkenyl unsaturation. Such groups are exemplified by vinyl, allyl, but-3-en-1-yl, and the like.

"Substituted alkenyl" refers to alkenyl groups having from 1 to 3 substituents, and preferably 1 to 2 substituents, selected from the group consisting of alkoxy, substituted alkoxy, acyl, acylamino, acyloxy, amino, substituted amino, aminoacyl, aryl, substituted aryl, aryloxy, substituted aryloxy, cyano, halogen, hydroxyl, nitro, carboxyl, carboxyl esters, cycloalkyl, substituted cycloalkyl, heteroaryl, substituted heteroaryl, heterocyclic, and substituted heterocyclic with the proviso that any hydroxyl substitution is not attached to a vinyl (unsaturated) carbon atom.

"Alkynyl" refers to alkynyl groups having from 2 to 6 carbon atoms and preferably 2 to 3 carbon atoms and having at least 1 and preferably from 1 to 2 sites of alkynyl unsaturation.

"Substituted alkynyl" refers to alkynyl groups having from 1 to 3 substituents, and preferably 1 to 2 substituents, selected from the group consisting of alkoxy, substituted alkoxy, acyl, acylamino, acyloxy, amino, substituted amino, aminoacyl, aryl, substituted aryl, aryloxy, substituted aryloxy, cyano, halogen, hydroxyl, nitro, carboxyl, carboxyl esters, cycloalkyl, substituted cycloalkyl, heteroaryl, substituted heteroaryl, heterocyclic, and substituted heterocyclic.

"Amino" refers to the group —NH$_2$.

"Cyano" refers to the group —CN.

"Substituted amino" refers to the group —NR$^{14}$R$^{15}$ where R$^{14}$ and R$^{15}$ are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, heteroaryl, substituted heteroaryl, heterocyclic, substituted heterocyclic and where R$^{14}$ and R$^{15}$ are joined, together with the nitrogen bound thereto to form a heterocyclic or substituted heterocyclic group provided that R$^{14}$ and R$^{15}$ are both not hydrogen. When R$^{14}$ is hydrogen and R$^{15}$ is alkyl, the substituted amino group is sometimes referred to herein as alkylamino. When R$^{14}$ and R$^{15}$ are alkyl, the substituted amino group is sometimes referred to herein as dialkylamino. When referring to a monosubstituted amino, it is meant that either R$^{14}$ or R$^{15}$ is hydrogen but not both. When referring to a disubstituted amino, it is meant that neither R$^{14}$ or R$^{15}$ is hydrogen.

"Acylamino" refers to the groups —NR$^{16}$C(O)alkyl, —NR$^{16}$C(O)substituted alkyl, —NR$^{16}$C(O)cycloalkyl, —NR$^{16}$C(O)substituted cycloalkyl, —NR$^{16}$C(O)alkenyl, —NR$^{16}$C(O)substituted alkenyl, —NR$^{16}$C(O)alkynyl, —NR$^{16}$C(O)substituted alkynyl, —NR$^{16}$C(O)aryl, —NR$^{16}$C(O)substituted aryl, —NR$^{16}$C(O)heteroaryl, —NR$^{16}$C(O)substituted heteroaryl, —NR$^{16}$C(O)heterocyclic, and —NR$^{16}$C(O)substituted heterocyclic where R$^{16}$ is hydrogen or alkyl and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Nitro" refers to the group —NO$_2$.

"Aryl" or "Ar" refers to a monovalent aromatic carbocyclic group of from 6 to 14 carbon atoms having a single ring (e.g., phenyl) or multiple condensed rings (e.g., naphthyl or anthryl) which condensed rings may or may not be aromatic (e.g., 2-benzoxazolinone, 2H-1,4-benzoxazin-3 (4H)-one-7-yl, and the like) provided that the point of attachment is at an aromatic carbon atom. Preferred aryls include phenyl and naphthyl.

"Substituted aryl" refers to aryl groups which are substituted with from 1 to 3 substituents, and preferably 1 to 2 substituents, selected from the group consisting of hydroxy, acyl, acylamino, acyloxy, alkyl, substituted alkyl, alkoxy, substituted alkoxy, alkenyl, substituted alkenyl, alkynyl, substituted alkynyl, amino, substituted amino, aminoacyl, aryl, substituted aryl, aryloxy, substituted aryloxy, carboxyl, carboxyl esters, cyano, thiol, alkylthio, substituted alkylthio, arylthio, substituted arylthio, heteroarylthio, substituted heteroarylthio, cycloalkylthio, substituted cycloalkylthio, heterocyclicthio, substituted heterocyclicthio, cycloalkyl, substituted cycloalkyl, cycloalkoxy, substituted cycloalkoxy, halo, nitro, heteroaryl, substituted heteroaryl, heterocyclic, substituted heterocyclic, heteroaryloxy, substituted heteroaryloxy, heterocyclyloxy, substituted heterocyclyloxy, amino sulfonyl (NH$_2$—SO$_2$—), and substituted amino sulfonyl.

"Aryloxy" refers to the group aryl-O— that includes, by way of example, phenoxy, naphthoxy, and the like.

"Substituted aryloxy" refers to substituted aryl-O— groups.

"Carboxyl" refers to —COOH or salts thereof.

"Carboxyl ester" refers to the groups —C(O)O-alkyl, —C(O)O-substituted alkyl, —C(O)O-aryl, and —C(O)O-substituted aryl wherein alkyl, substituted alkyl, aryl and substituted aryl are as defined herein.

"Cycloalkyl" refers to cyclic alkyl groups of from 3 to 10 carbon atoms having single or multiple cyclic rings including, by way of example, adamantyl, cyclopropyl, cyclobutyl, cyclopentyl, cyclooctyl and the like.

"Spirocycloalkyl" refers to cyclic groups from 3 to 10 carbon atoms having a cycloalkyl ring with a spiro union (the union formed by a single atom which is the only common member of the rings) as exemplified by the following structure:

"Substituted cycloalkyl" and "substituted cycloalkenyl" refers to an cycloalkyl or cycloalkenyl group, having from 1 to 5 substituents selected from the group consisting of oxo (=O), thioxo (=S), alkyl, substituted alkyl, alkoxy, substituted alkoxy, acyl, acylamino, acyloxy, amino, substituted amino, aminoacyl, aryl, substituted aryl, aryloxy, substituted aryloxy, cyano, halogen, hydroxyl, nitro, carboxyl, carboxyl esters, cycloalkyl, substituted cycloalkyl, heteroaryl, substituted heteroaryl, heterocyclic, and substituted heterocyclic.

"Cycloalkoxy" refers to —O-cycloalkyl groups.

"Substituted cycloalkoxy" refers to —O-substituted cycloalkyl groups.

"Halo" or "halogen" refers to fluoro, chloro, bromo and iodo and preferably is fluoro or chloro.

"Hydroxy" refers to the group —OH.

"Heteroaryl" refers to an aromatic group of from 1 to 10 carbon atoms and 1 to 4 heteroatoms selected from the group consisting of oxygen, nitrogen and sulfur within the ring. Such heteroaryl groups can have a single ring (e.g., pyridinyl or furyl) or multiple condensed rings (e.g., indolizinyl or benzothienyl) wherein the condensed rings may or may not be aromatic and/or contain a heteroatom provided that the point of attachment is through an atom of the aromatic heteroaryl group. Preferred heteroaryls include pyridinyl, pyrrolyl, indolyl, thiophenyl, and furanyl.

"Substituted heteroaryl" refers to heteroaryl groups that are substituted with from 1 to 3 substituents selected from the same group of substituents defined for substituted aryl.

"Heteroaryloxy" refers to the group —O-heteroaryl and "substituted heteroaryloxy" refers to the group —O-substituted heteroaryl.

"Heterocycle" or "heterocyclic" or "heterocycloalkyl" or "heterocyclyl" refers to a saturated or unsaturated group having a single ring or multiple condensed rings, from 1 to 10 carbon atoms and from 1 to 4 hetero atoms selected from the group consisting of nitrogen, sulfur or oxygen within the ring wherein, in fused ring systems, one or more the rings can be cycloalkyl, aryl or heteroaryl provided that the point of attachment is through the heterocyclic ring.

"Substituted heterocyclic" or "substituted heterocycloalkyl" or "substituted heterocyclyl" refers to heterocyclyl groups that are substituted with from 1 to 3 of the same substituents as defined for substituted cycloalkyl.

Examples of heterocyclyls and heteroaryls include, but are not limited to, azetidine, pyrrole, imidazole, pyrazole, pyridine, pyrazine, pyrimidine, pyridazine, indolizine, isoindole, indole, dihydroindole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, indoline, phthalimide, 1,2,3,4-tetrahydro-isoquinoline, 4,5,6,7-tetrahydrobenzo[b]thiophene, thiazole, thiazolidine, thiophene, benzo[b]thiophene, morpholinyl, thiomorpholinyl (also referred to as thiamorpholinyl), piperidinyl, pyrrolidine, tetrahydrofuranyl, and the like.

"Thiol" refers to the group —SH.

"Alkylthio" or "alkylthioether" or "thioalkoxy" refers to the group —S-alkyl.

"Substituted alkylthio" or "substituted alkylthioether" or "substituted thioalkoxy" refers to the group —S-substituted alkyl.

"Arylthio" refers to the group —S-aryl, where aryl is defined above.

"Substituted arylthio" refers to the group —S-substituted aryl, where substituted aryl is defined above.

"Heteroarylthio" refers to the group —S-heteroaryl, where heteroaryl is as defined above.

"Substituted heteroarylthio" refers to the group —S-substituted heteroaryl, where substituted heteroarylthio is defined above.

"Heterocyclicthio" refers to the group —S-heterocyclic and "substituted heterocyclicthio" refers to the group —S-substituted heterocyclic, where heterocyclic and substituted heterocyclic.

"Heterocyclyloxy" refers to the group heterocyclyl-O— and "substituted heterocyclyl-O— refers to the group substituted heterocyclyl-O— where heterocyclyl and substituted heterocyclyl are as defined above.

"Cycloalkylthio" refers to the group —S-cycloalkyl and "substituted cycloalkylthio" refers to the group —S-substituted cycloalkyl, where cycloalkyl and substituted cycloalkyl are as defined above.

"Arylalkyl" refers to an alkyl group substituted with an aryl group, where alkyl and aryl are as defined herein. This group is alternatively represented as -alkylene-aryl.

"Heteroarylalkyl" refers to an alkyl group substituted with a heteroaryl group, where alkyl and heteroaryl are as defined herein. This group is alternatively represented as -alkylene-heteroaryl.

"Cycloalkylalkyl" refers to an alkyl group substituted with a cycloalkyl group, where alkyl and cycloalkyl are as defined herein.

"Biological activity" as used herein refers to an inhibition concentration when tested in at least one of the assays outlined in Example 3.

As used herein, the term "pharmaceutically acceptable salts" refers to the nontoxic acid or alkaline earth metal salts of the compounds of formulae I, II, and/or III. These salts can be prepared in situ during the final isolation and purification of the compounds of formulae I, II, and/or III, or by separately reacting the base or acid functions with a suitable organic or inorganic acid or base, respectively. Representative salts include, but are not limited to, the following: acetate, adipate, alginate, citrate, aspartate, benzoate, benzenesulfonate, bisulfate, butyrate, camphorate, camphorsulfonate, digluconate, cyclopentanepropionate, dodecylsulfate, ethanesulfonate, glucoheptanoate, glycerophosphate, hemisulfate, heptanoate, hexanoate, fumarate, hydrochloride, hydrobromide, hydroiodide, 2-hydroxyethanesulfonate, lactate, maleate, methanesulfonate, nicotinate, 2-napthalenesulfonate, oxalate, pamoate, pectinate, persulfate, 3-phenylproionate, picrate, pivalate, propionate, succinate, sulfate, tartrate, thiocyanate, p-toluenesulfonate and undecanoate. Also, the basic nitrogen-containing groups can be quaternized with such agents as alkyl halides, such as methyl, ethyl, propyl, and butyl chloride, bromides, and iodides; dialkyl sulfates like dimethyl, diethyl, dibutyl, and diamyl sulfates, long chain halides such as decyl, lauryl, myristyl and stearyl chlorides, bromides and iodides, aralkyl halides like benzyl and phenethyl bromides, and others. Water or oil-soluble or dispersible products are thereby obtained.

Examples of acids that may be employed to form pharmaceutically acceptable acid addition salts include such inorganic acids as hydrochloric acid, sulfuric acid and phosphoric acid and such organic acids as oxalic acid, maleic acid, methanesulfonic acid, succinic acid and citric acid. Basic addition salts can be prepared in situ during the final isolation and purification of the compounds of formulae I, II, and/or III, or separately by reacting carboxylic acid moieties with a suitable base such as the hydroxide, carbonate or bicarbonate of a pharmaceutically acceptable metal cation or with ammonia, or an organic primary, secondary or tertiary amine. Pharmaceutically acceptable salts include, but are not limited to, cations based on the alkali and alkaline earth metals, such as sodium, lithium, potassium, calcium, magnesium, aluminum salts and the like, as well as ammonium, quaternary ammonium, and amine cations, including, but not limited to ammonium, tetramethylammonium, tetraethylammonium, methylamine, dimethylamine, trimethylamine, triethylamine, ethylamine, and the like. Other representative organic amines useful for the formation of base addition salts include diethylamine, ethylenediamine, ethanolamine, diethanolamine, piperazine and the like.

As used herein, the term "pharmaceutically acceptable ester" refers to esters which may hydrolyze in vivo and include those that break down in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Representative examples of particular esters include, but are not limited to, formates, acetates, propionates, butyrates, acrylates and ethylsuccinates.

The term "pharmaceutically acceptable prodrug" as used herein refers to those prodrugs of the compounds of the present invention which are, within the scope of sound medical judgment, suitable for use in contact with the tissues of humans and lower animals without undue toxicity, irritation, allergic response, and the like, commensurate with a reasonable benefit/risk ratio, and effective for their intended use, as well as the zwitterionic forms, where possible, of the compounds of the invention. The term "prodrug" refers to compounds that are rapidly transformed in vivo to yield the parent compound of the above formula, for example by hydrolysis in blood. A discussion is provided in T. Higuchi and V. Stella, Pro-drugs as Novel Delivery Systems, Vol. 14 of the A.C.S. Symposium Series, and in Edward B. Roche, ed., Bioreversible Carriers in Drug Design, American Pharmaceutical Association and Pergamon Press, 1987, both of which are incorporated herein by reference.

As used herein "anticancer agents" or "agent for the treatment of cancer" refers to agents that include, by way of example only, agents that induce apoptosis; polynucleotides (e.g., ribozymes); polypeptides (e.g., enzymes); drugs; biological mimetics; alkaloids; alkylating agents; antitumor antibiotics; antimetabolites; hormones; platinum compounds; monoclonal antibodies conjugated with anticancer drugs, toxins, and/or radionuclides; biological response modifiers (e.g. interferons and interleukins, etc.); adoptive immunotherapy agents; hematopoietic growth factors; agents that induce tumor cell differentiation (e.g. all-trans-retinoic acid, etc.); gene therapy reagents; antisense therapy reagents and nucleotides; tumor vaccines; inhibitors of angiogenesis, and the like. Numerous other agents are well within the purview of one of skill in the art It is understood that in all substituted groups defined above, polymers arrived at by defining substituents with further substituents to themselves (e.g., substituted aryl having a substituted aryl group as a substituent which is itself substituted with a substituted aryl group, etc.) are not intended for inclusion herein. In such cases, the maximum number of such substituents is three. That is to say that each of the above definitions is constrained by a limitation that, for example, substituted aryl groups are limited to -substituted aryl-(substituted aryl)-substituted aryl.

Similarly, it is understood that the above definitions are not intended to include impermissible substitution patterns (e.g., methyl substituted with 5 fluoro groups or a hydroxyl group alpha to ethenylic or acetylenic unsaturation). Such impermissible substitution patterns are well known to the skilled artisan.

Compounds of this invention may exhibit stereoisomerism by virtue of the presence of one or more asymmetric or chiral centers in the compounds. The present invention contemplates the various stereoisomers and mixtures thereof. Certain of the compounds of the invention comprise asymmetrically substituted carbon atoms. Such asymmetrically substituted carbon atoms can result in the compounds of the invention comprising mixtures of stereoisomers at a particular asymmetrically substituted carbon atom or a single stereoisomer. As a result, racemic mixtures, mixtures of diastereomers, single enantiomer, as well as single diastereomers of the compounds of the invention are included in the present invention. The terms "S" and "R" configuration, as used herein, are as defined by the IUPAC 1974 "RECOMMENDATIONS FOR SECTION E, FUNDAMENTAL STEREOCHEMISTRY," Pure Appl. Chem. 45:13-30, 1976. Desired enantiomers can be obtained by chiral synthesis from commercially available chiral starting materials by methods well known in the art, or may be obtained from mixtures of the enantiomers by separating the desired enantiomer by using known techniques.

Compounds of this invention may also exhibit geometrical isomerism. Geometrical isomers include the cis and trans forms of compounds of the invention having alkenyl or alkenylenyl moieties. The present invention comprises the individual geometrical isomers and stereoisomers and mixtures thereof.

Compound Preparation

The compounds of this invention can be prepared from readily available starting materials using the following general methods and procedures. It will be appreciated that where typical or preferred process conditions (i.e., reaction temperatures, times, mole ratios of reactants, solvents, pressures) are given, other process conditions can also be used unless otherwise stated. Optimum reaction conditions may vary with the particular reactants or solvent used, but such conditions can be determined by one skilled in the art by routine optimization procedures.

Additionally, as will be apparent to those skilled in the art, conventional protecting groups may be necessary to prevent certain functional groups from undergoing undesired reactions. Suitable protecting groups for various functional groups as well as suitable conditions for protecting and deprotecting particular functional groups are well known in the art. For example, numerous protecting groups are described in T. W. Greene and P. G. M. Wuts, Protecting Groups in Organic Synthesis, Second Edition, Wiley, New York, 1991, and references cited therein.

Compounds in the present invention may be better understood by the following synthetic Scheme that illustrate methods for the synthesis of compounds of the invention. Unless otherwise indicated, the reagents used in the following examples are commercially available and may be purchased from vendors such as Sigma-Aldrich Company, Inc. (Milwaukee, Wis., USA).

Compounds of the invention may be synthesized according to Scheme 1 below.

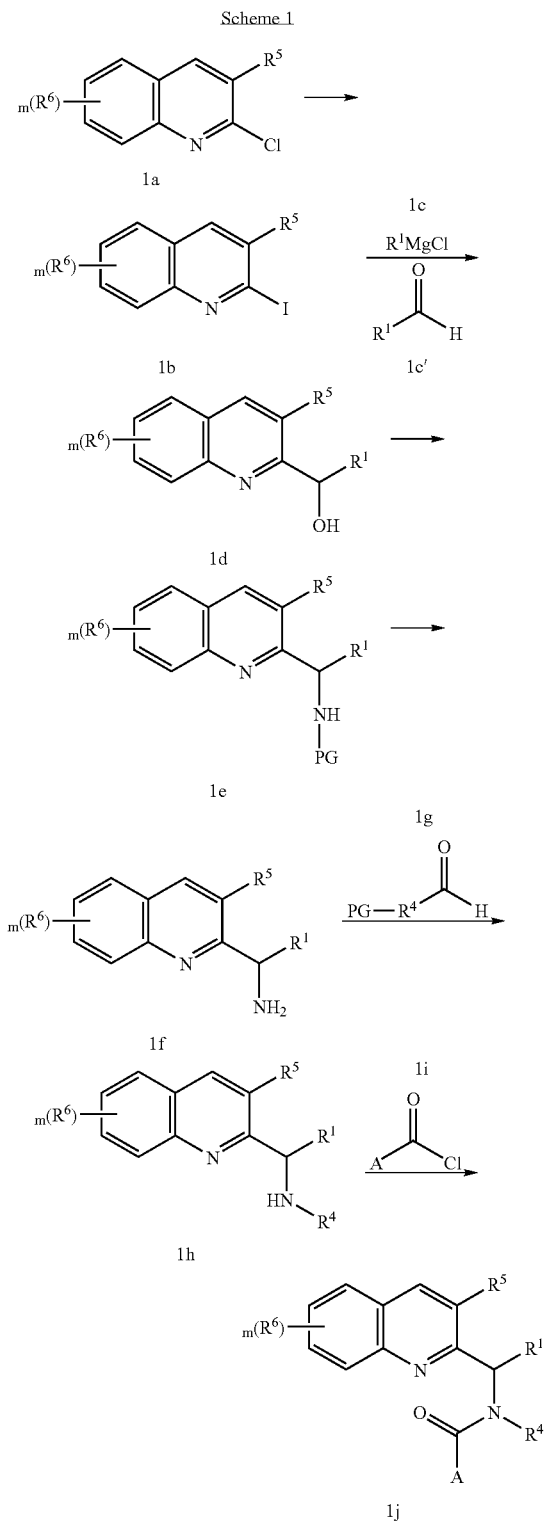

R¹, R⁴, R⁵ R⁶, m, and A are as defined herein.
each PG independently refers to an amino protecting group such as phthalimide.

Specifically, in Scheme 1, an appropriately substituted chloroquinoline derivative, 1a, is combined with an excess of sodium iodide typically from about 2 to 20 equivalents and preferably about 10 equivalents in a suitable inert solvent, such as methyl ethyl ketone, acetone, and the like. An excess of hydroiodic acid is then added. In one embodiment, the resulting mixture is initially heated at elevated temperatures of from about 50 to about 80° C. and preferably at reflux for a period of time of from about 2 to 12 hours followed by maintaining the reaction at room temperature for a period of from about 12 to 24 hours. Upon substantial completion of the reaction, the resulting iodoquinoline derivative 1b can be recovered and optionally purified by conventional methods such as precipitation, filtration, evaporation, crystallization, chromatography and the like. Alternatively, compound 1b can be used directly in the next step without purification and/or isolation.

Next, iodoquinoline derivative, 1b, is dissolved while stirring in a suitable solvent such as tetrahydrofuran, glyme, and the like while maintaining the temperature of the solution at from about −50 to about −80° C. Stirring is continued at this temperature for approximately 0.1 to 1 hour and then an excess, e.g., three equivalents, of an organomagnesium chloride, compound 1c, is added into the solution. The addition of compound 1c is conducted over a prolonged period of time such as one hour. An excess of an aldehyde compound, 1c', that corresponds to the organomagnesium chloride is then added to the reaction mixture and the resulting mixture is allowed to warm to room temperature over approximately one hour. The resulting alcohol, 1d, can be recovered by conventional methods such as precipitation, filtration, evaporation, crystallization, chromatography and the like. Alternatively, compound 1d can be used directly in the next step without purification and/or isolation.

Protected amine, 1e, is prepared by reaction of alcohol, 1d, with an excess, e.g., about 3 equivalents, of a suitable amine protecting group, such as phthalimide. To the reaction is then added an excess of both triphenylphosphine and diisopropyl diazodicarboxylate (DIAD) while maintaining the reaction at a temperature of from about −20 to about 10° C. The reaction is allowed to warm to room temperature and continued until it is substantially complete, typically 2 to 24 hours. The resulting protected amine 1e is then recovered and optionally purified by conventional methods such as precipitation, filtration, evaporation, crystallization, chromatography and the like. Alternatively, compound 1e can be used directly in the next step without purification and/or isolation.

The protecting group is then removed by conventional techniques to provide for amine 1f which is then recovered and optionally purified by conventional methods such as precipitation, filtration, evaporation, crystallization, chromatography and the like. Alternatively, compound 1f can be used directly in the next step without purification and/or isolation.

Amine 1f is reacted under conventional reductive amination conditions with aldehyde 1 g to provide for substituted amine 1h which is then recovered and optionally purified by conventional methods such as precipitation, filtration, evaporation, crystallization, chromatography and the like. Alternatively, compound 1h can be used directly in the next step without purification and/or isolation.

Substituted amine 1h is then reacted under conventional amidation conditions with acyl chloride 1i. Any protecting groups remaining on the resulting amide product, 1j, can be removed by conventional methods and the product can be recovered and purified by conventional methods such as precipitation, filtration, evaporation, crystallization, chromatography and the like.

Quinoline compounds, 1a, are either commercially available or can be prepared from an appropriately substituted aniline compound as shown in Scheme 2 below wherein, for illustrative purposes only, m is one and $R^6$ is chloro.

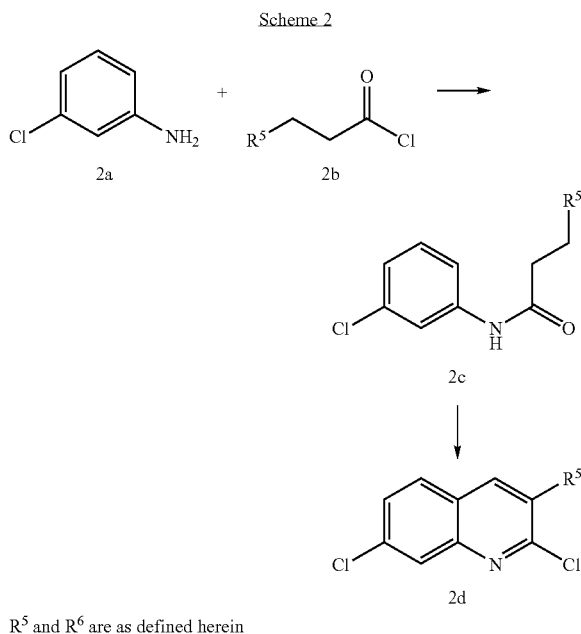

$R^5$ and $R^6$ are as defined herein

Specifically, in Scheme 2, a commercially available aniline, compound 2a, is amidated under conventional conditions with a slight excess (~10%) of 3-substituted propionyl chloride, 2b, to provided for amide 2c which can be recovered and purified by conventional methods such as precipitation, filtration, evaporation, crystallization, chromatography and the like. Next, an excess of phosphorous oxytrichloride and 1 to 2 equivalents of dimethyl formamide (DMF) is stirred for typically about an hour while maintaining the reaction at a temperature of from about −20 to about 10° C. Amide 2c is then added by stirring and the reaction allowed to warm to room temperature, then heated to from about 60 to about 90° C. and continued until it is substantially complete, typically 2 to 24 hours.

The resulting protected quinoline 2d is then recovered and optionally purified by conventional methods such as precipitation, filtration, evaporation, crystallization, chromatography and the like. Alternatively, compound 2d can be used directly in the next step without purification and/or isolation.

Pharmaceutical Formulations

When employed as pharmaceuticals, the compounds of the subject invention are usually administered in the form of pharmaceutical compositions. These compounds can be administered by a variety of routes including oral, parenteral, transdermal, topical, rectal, and intranasal. These compounds are effective as both injectable and oral compositions. Such compositions are prepared in a manner well known in the pharmaceutical art and comprise at least one active compound.

This invention also includes pharmaceutical compositions which contain, as the active ingredient, one or more of the compounds of the subject invention above associated with pharmaceutically acceptable carriers. In making the compositions of this invention, the active ingredient is usually mixed with an excipient, diluted by an excipient or enclosed within such a carrier which can be in the form of a capsule, sachet, paper or other container. The excipient employed is typically an excipient suitable for administration to human subjects or other mammals. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders.

In preparing a formulation, it may be necessary to mill the active compound to provide the appropriate particle size prior to combining with the other ingredients. If the active compound is substantially insoluble, it ordinarily is milled to a particle size of less than 200 mesh. If the active compound is substantially water soluble, the particle size is normally adjusted by milling to provide a substantially uniform distribution in the formulation, e.g., about 40 mesh.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, sterile water, syrup, and methyl cellulose. The formulations can additionally include: lubricating agents such as talc, magnesium stearate, and mineral oil, wetting agents, emulsifying and suspending agents, preserving agents such as methyl- and propylhydroxy-benzoates, sweetening agents, and flavoring agents. The compositions of the invention can be formulated so as to provide quick, sustained or delayed release of the active ingredient after administration to the patient by employing procedures known in the art.

The quantity of active component, that is the compound according to the subject invention, in the pharmaceutical composition and unit dosage form thereof may be varied or adjusted widely depending upon the particular application, the potency of the particular compound and the desired concentration.

The compositions are preferably formulated in a unit dosage form, each dosage containing from about 1 to about 500 mg, usually about 5 to about 100 mg, occasionally about 10 to about 30 mg, of the active ingredient. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient. Preferably, the compound of the subject invention above is employed at no more than about 20 weight percent of the pharmaceutical composition, more preferably no more than about 15 weight percent, with the balance being pharmaceutically inert carrier(s).

The active compound is effective over a wide dosage range and is generally administered in a pharmaceutically or therapeutically effective amount. It will be understood, however, that the amount of the compound actually administered will be determined by a physician, in the light of the relevant circumstances, including the condition to be treated, the severity of the condition being treated, the chosen route of administration, the actual compound administered, the age, weight, and response of the individual patient, the severity of the patient's symptoms, and the like.

In therapeutic use for treating, or combating, cancer in warm-blooded animals, the compounds or pharmaceutical compositions thereof will be administered by any appropriate route, such as orally, topically, transdermally, and/or parenterally at a dosage to obtain and maintain a concentration, that is, an amount, or blood-level of active component in the animal undergoing treatment that will be therapeutically effective. Generally, such therapeutically effective amount of dosage of active component (i.e., an effective dosage) will be in the range of about 5 μg to about 50 mg per kilogram body weight, more preferably about 1.0 to about 50 mg/kg of body weight/day.

For preparing solid compositions such as tablets, the principal active ingredient is mixed with a pharmaceutical excipient to form a solid preformulation composition containing a homogeneous mixture of a compound of the present invention. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation is then subdivided into unit dosage forms of the type described above containing from, for example, 0.1 to about 500 mg of the active ingredient of the present invention.

The tablets or pills of the present invention may be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the novel compositions of the present invention may be incorporated for administration orally or by injection include aqueous solutions, suitably flavored syrups, aqueous or oil suspensions, and flavored emulsions with edible oils such as corn oil, cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. Preferably the compositions are administered by the oral or nasal respiratory route for local or systemic effect. Compositions in preferably pharmaceutically acceptable solvents may be nebulized by use of inert gases. Nebulized solutions may be inhaled directly from the nebulizing device or the nebulizing device may be attached to a face mask tent, or intermittent positive pressure breathing machine. Solution, suspension, or powder compositions may be administered, preferably orally or nasally, from devices which deliver the formulation in an appropriate manner.

The following formulation examples illustrate representative pharmaceutical compositions of the present invention.

Formulation Example 1

Hard gelatin capsules containing the following ingredients are prepared:

| Ingredient | Quantity (mg/capsule) |
| --- | --- |
| Active Ingredient | 30.0 |
| Starch | 305.0 |
| Magnesium stearate | 5.0 |

The above ingredients are mixed and filled into hard gelatin capsules in 340 mg quantities.

Formulation Example 2

A tablet formula is prepared using the ingredients below:

| Ingredient | Quantity (mg/tablet) |
| --- | --- |
| Active Ingredient | 25.0 |
| Cellulose, microcrystalline | 200.0 |
| Colloidal silicon dioxide | 10.0 |
| Stearic acid | 5.0 |

The components are blended and compressed to form tablets, each weighing 240 mg.

Formulation Example 3

A dry powder inhaler formulation is prepared containing the following components:

| Ingredient | Weight % |
| --- | --- |
| Active Ingredient | 5 |
| Lactose | 95 |

The active ingredient is mixed with the lactose and the mixture is added to a dry powder inhaling appliance.

Formulation Example 4

Tablets, each containing 30 mg of active ingredient, are prepared as follows

| Ingredient | Quantity (mg/tablet) |
| --- | --- |
| Active Ingredient | 30.0 mg |
| Starch | 45.0 mg |
| Microcrystalline cellulose | 35.0 mg |
| Polyvinylpyrrolidone (as 10% solution in sterile water) | 4.0 mg |
| Sodium carboxymethyl starch | 4.5 mg |
| Magnesium stearate | 0.5 mg |
| Talc | 1.0 mg |
| Total | 120 mg |

The active ingredient, starch and cellulose are passed through a No. 20 mesh U.S. sieve and mixed thoroughly. The solution of polyvinylpyrrolidone is mixed with the resultant powders, which are then passed through a 16 mesh U.S. sieve. The granules so produced are dried at 50° C. to 60° C. and passed through a 16 mesh U.S. sieve. The sodium carboxymethyl starch, magnesium stearate, and talc, previously passed through a No. 30 mesh U.S. sieve, are then added to the granules which, after mixing, are compressed on a tablet machine to yield tablets each weighing 120 mg.

Formulation Example 5

Capsules, each containing 40 mg of medicament are made as follows:

| Ingredient | Quantity (mg/capsule) |
| --- | --- |
| Active Ingredient | 40.0 mg |
| Starch | 109.0 mg |
| Magnesium stearate | 1.0 mg |
| Total | 150.0 mg |

The active ingredient, starch and magnesium stearate are blended, passed through a No. 20 mesh U.S. sieve, and filled into hard gelatin capsules in 150 mg quantities.

Formulation Example 6

Suppositories, each containing 25 mg of active ingredient are made as follows:

| Ingredient | Amount |
| --- | --- |
| Active Ingredient | 25 mg |
| Saturated fatty acid glycerides to | 2,000 mg |

The active ingredient is passed through a No. 60 mesh U.S. sieve and suspended in the saturated fatty acid glycerides previously melted using the minimum heat necessary. The mixture is then poured into a suppository mold of nominal 2.0 g capacity and allowed to cool.

Formulation Example 7

Suspensions, each containing 50 mg of medicament per 5.0 ml dose are made as follows:

| Ingredient | Amount |
| --- | --- |
| Active Ingredient | 50.0 mg |
| Xanthan gum | 4.0 mg |
| Sodium carboxymethyl cellulose (11%) Microcrystalline cellulose (89%) | 50.0 mg |
| Sucrose | 1.75 g |
| Sodium benzoate | 10.0 mg |
| Flavor and Color | q.v. |
| Purified water to | 5.0 ml |

The active ingredient, sucrose and xanthan gum are blended, passed through a No. 10 mesh U.S. sieve, and then mixed with a previously made solution of the microcrystalline cellulose and sodium carboxymethyl cellulose in water. The sodium benzoate, flavor, and color are diluted with some of the water and added with stirring. Sufficient water is then added to produce the required volume.

Formulation Example 8

| Ingredient | Quantity (mg/capsule) |
| --- | --- |
| Active Ingredient | 15.0 mg |
| Starch | 407.0 mg |
| Magnesium stearate | 3.0 mg |
| Total | 425.0 mg |

The active ingredient, starch, and magnesium stearate are blended, passed through a No. 20 mesh U.S. sieve, and filled into hard gelatin capsules in 425.0 mg quantities.

Formulation Example 9

A subcutaneous formulation may be prepared as follows:

| Ingredient | Quantity |
| --- | --- |
| Active Ingredient | 5.0 mg |
| Corn Oil | 1.0 ml |

Formulation Example 10

A topical formulation may be prepared as follows:

| Ingredient | Quantity |
| --- | --- |
| Active Ingredient | 1-10 g |
| Emulsifying Wax | 30 g |
| Liquid Paraffin | 20 g |
| White Soft Paraffin | to 100 g |

The white soft paraffin is heated until molten. The liquid paraffin and emulsifying wax are incorporated and stirred until dissolved. The active ingredient is added and stirring is continued until dispersed. The mixture is then cooled until solid.

Formulation Example 11

An intravenous formulation may be prepared as follows:

| Ingredient | Quantity |
| --- | --- |
| Active Ingredient | 250 mg |
| Isotonic saline | 1000 ml |

Another preferred formulation employed in the methods of the present invention employs transdermal delivery devices ("patches"). Such transdermal patches may be used to provide continuous or discontinuous infusion of the compounds of the present invention in controlled amounts. The construction and use of transdermal patches for the delivery of pharmaceutical agents is well known in the art. See, e.g., U.S. Pat.

No. 5,023,252, herein incorporated by reference. Such patches may be constructed for continuous, pulsatile, or on demand delivery of pharmaceutical agents.

Frequently, it will be desirable or necessary to introduce the pharmaceutical composition to the brain, either directly or indirectly. Direct techniques usually involve placement of a drug delivery catheter into the host's ventricular system to bypass the blood-brain barrier. One such implantable delivery system used for the transport of biological factors to specific anatomical regions of the body is described in U.S. Pat. No. 5,011,472 which is herein incorporated by reference.

Indirect techniques, which are generally preferred, usually involve formulating the compositions to provide for drug latentiation by the conversion of hydrophilic drugs into lipid-soluble drugs. Latentiation is generally achieved through blocking of the hydroxy, carbonyl, sulfate, and primary amine groups present on the drug to render the drug more lipid soluble and amenable to transportation across the blood-brain barrier. Alternatively, the delivery of hydrophilic drugs may be enhanced by intra-arterial infusion of hypertonic solutions which can transiently open the blood-brain barrier.

Other suitable formulations for use in the present invention can be found in Remington's Pharmaceutical Sciences, Mace Publishing Company, Philadelphia, Pa., 17th ed. (1985).

Dosage and Administration

As noted above, the compounds described herein are suitable for use in a variety of drug delivery systems described above. Additionally, in order to enhance the in vivo serum half-life of the administered compound, the compounds may be encapsulated, introduced into the lumen of liposomes, prepared as a colloid, or other conventional techniques may be employed which provide an extended serum half-life of the compounds. A variety of methods are available for preparing liposomes, as described in, e.g., Szoka, et al., U.S. Pat. Nos. 4,235,871, 4,501,728 and 4,837,028 each of which is incorporated herein by reference.

Compounds of the instant invention are useful for inhibiting the activity of KSP Kinesin. In one aspect, the disorder that is mediated, at least in part by KSP is a cellular proliferative disorder. The term "cellular proliferative disorder" or "cell proliferative disorder" refers to diseases including, for example, cancer, tumor, hyperplasia, restenosis, cardiac hypertrophy, immune disorder and inflammation. The present invention provides methods of treating a human or animal subject in need of such treatment, comprising administering to the subject a therapeutically effective amount of a compound of formulae I-III, either alone or in combination with other anticancer agents.

The compounds of the invention are useful in vitro or in vivo in inhibiting the growth of cancer cells. The term "cancer" refers to cancer diseases including, for example, lung and bronchus; prostate; breast; pancreas; colon and rectum; thyroid; stomach; liver and intrahepatic bile duct; kidney and renal pelvis; urinary bladder; uterine corpus; uterine cervix; ovary; multiple myeloma; esophagus; acute myelogenous leukemia; chronic myelognous leukemia; lymphocytic leukemia; myeloid leukemia; brain; oral cavity and pharynx; larynx; small intestine; non-hodgkin lymphoma; melanoma; and villous colon adenoma.

Cancer also includes tumors or neoplasms selected from the group consisting of carcinomas, adenocarcinomas and sarcomas.

Additionally, the type of cancer can be selected from the group consisting of growth of solid tumors/malignancies, myxoid and round cell carcinoma, locally advanced tumors, human soft tissue carcinoma, cancer metastases, squamous cell carcinoma, esophageal squamous cell carcinoma, oral carcinoma, cutaneous T cell lymphoma, Hodgkin's lymphoma, non-Hodgkin's lymphoma, cancer of the adrenal cortex, ACTH-producing tumors, nonsmall cell cancers, breast cancer, gastrointestinal cancers, urological cancers, malignancies of the female genital tract, malignancies of the male genital tract, kidney cancer, brain cancer, bone cancers, skin cancers, thyroid cancer, retinoblastoma, neuroblastoma, peritoneal effusion, malignant pleural effusion, mesothelioma, Wilms's tumors, gall bladder cancer, trophoblastic neoplasms, hemangiopericytoma, and Kaposi's sarcoma.

A compound or composition of this invention may be administered to the mammal by a suitable route, such as orally, intravenously, parenterally, transdermally, topically, rectally, or intranasally.

Mammals include, for example, humans and other primates, pet or companion animals, such as dogs and cats, laboratory animals, such as rats, mice and rabbits, and farm animals, such as horses, pigs, sheep, and cattle.

Tumors or neoplasms include growths of tissue cells in which the multiplication of the cells is uncontrolled and progressive. Some such growths are benign, but others are termed "malignant" and can lead to death of the organism. Malignant neoplasms or "cancers" are distinguished from benign growths in that, in addition to exhibiting aggressive cellular proliferation, they can invade surrounding tissues and metastasize. Moreover, malignant neoplasms are characterized in that they show a greater loss of differentiation (greater "dedifferentiation") and organization relative to one another and to surrounding tissues. This property is called "anaplasia."

Compounds having the desired biological activity may be modified as necessary to provide desired properties such as improved pharmacological properties (e.g., in vivo stability, bio-availability), or the ability to be detected in diagnostic applications. Stability can be assayed in a variety of ways such as by measuring the half-life of the compounds during incubation with peptidases or human plasma or serum.

For diagnostic purposes, a wide variety of labels may be linked to the compounds, which may provide, directly or indirectly, a detectable signal. Thus, the compounds and/or compositions of the subject invention may be modified in a variety of ways for a variety of end purposes while still retaining biological activity. In addition, various reactive sites may be introduced for linking to particles, solid substrates, macromolecules, and the like.

Labeled compounds can be used in a variety of in vivo or in vitro applications. A wide variety of labels may be employed, such as radionuclides (e.g., gamma-emitting radioisotopes such as technetium-99 or indium-111), fluorescers (e.g., fluorescein), enzymes, enzyme substrates, enzyme cofactors, enzyme inhibitors, chemiluminescent compounds, bioluminescent compounds, and the like. Those of ordinary skill in the art will know of other suitable labels for binding to the complexes, or will be able to ascertain such using routine experimentation. The binding of these labels is achieved using standard techniques common to those of ordinary skill in the art.

Pharmaceutical compositions of the invention are suitable for use in a variety of drug delivery systems. Suitable formulations for use in the present invention are found in Remington's Pharmaceutical Sciences, Mace Publishing Company, Philadelphia, Pa., 17th ed. (1985).

The amount administered to the patient will vary depending upon what is being administered, the purpose of the administration, such as prophylaxis or therapy, the state of the patient, the manner of administration, and the like. In therapeutic applications, compositions are administered to a patient already suffering from a disease in an amount sufficient to cure or at least partially arrest the progression or symptoms of the disease and its complications. An amount adequate to accomplish this is defined as "therapeutically effective dose." Amounts effective for this use will depend on the disease condition being treated as well as by the judgment of the attending clinician depending upon factors such as the severity of the disease, disorder or condition, the age, weight and general condition of the patient, and the like.

The compounds administered to a patient are typically in the form of pharmaceutical compositions described above. These compositions may be sterilized by conventional sterilization techniques, or may be sterile filtered. The resulting aqueous solutions may be packaged for use as is, or lyophilized, the lyophilized preparation being combined with a sterile aqueous carrier prior to administration. The pH of the compound preparations typically will be between about 3 and 11, more preferably from about 5 to 9 and most preferably from about 7 to 8. It will be understood that use of certain of the foregoing excipients, carriers, or stabilizers will result in the formation of pharmaceutical salts.

The therapeutic dosage of the compounds and/or compositions of the present invention will vary according to, for example, the particular use for which the treatment is made, the manner of administration of the compound, the health and condition of the patient, and the judgment of the prescribing physician. For example, for oral administration, the dose will typically be in the range of about 5 μg to about 50 mg per kilogram body weight per day, preferably about 1 mg to about 10 mg per kilogram body weight per day. In the alternative, for intravenous administration, the dose will typically be in the range of about 5 μg to about 50 mg per kilogram body weight, preferably about 500 μg to about 5000 μg per kilogram body weight. Alternative routes of administration contemplated include, but are not limited to, intranasal, transdermal, inhaled, subcutaneous and intramuscular. Effective doses can be extrapolated from dose-response curves derived from in vitro or animal model test systems.

In general, the compounds and/or compositions of the subject invention will be administered in a therapeutically effective amount by any of the accepted modes of administration for agents that serve similar utilities. Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds that exhibit large therapeutic indices are preferred.

The data obtained from the cell culture assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilized. For any compound and/or composition used in the method of the invention, the therapeutically effective dose can be estimated initially from cell culture assays. A dose may be formulated in animal models to achieve a circulating plasma concentration range which includes the $IC_{50}$ (the concentration of the test compound which achieves a half-maximal inhibition of activity) as determined in cell culture. Such information can be used to more accurately determine useful doses in humans. Levels in plasma may be measured, for example, by high performance liquid chromatography.

The following synthetic and biological examples are offered to illustrate this invention and are not to be construed in any way as limiting the scope of this invention.

EXAMPLES

Referring to the examples that follow, compounds of the present invention were synthesized using the methods described herein, or other methods, which are well known in the art.

The compounds and/or intermediates were characterized by high performance liquid chromatography (HPLC) using a Waters Millenium chromatography system with a 2690 Separation Module (Milford, Mass.). The analytical columns were Alltima C-18 reversed phase, 4.6×250 mm from Alltech (Deerfield, Ill.). A gradient elution was used, typically starting with 5% acetonitrile/95% water and progressing to 100% acetonitrile over a period of 40 minutes. All solvents contained 0.1% trifluoroacetic acid (TFA). Compounds were detected by ultraviolet light (UV) absorption at either 220 or 254 nm. HPLC solvents were from Burdick and Jackson (Muskegan, Mich.), or Fisher Scientific (Pittsburgh, Pa.). In some instances, purity was assessed by thin layer chromatography (TLC) using glass or plastic backed silica gel plates, such as, for example, Baker-Flex Silica Gel 1 B2-F flexible sheets. TLC results were readily detected visually under ultraviolet light, or by employing well known iodine vapor and other various staining techniques.

Mass spectrometric analysis was performed on one of two LCMS instruments: a Waters System (Alliance HT HPLC and a Micromass ZQ mass spectrometer; Column: Eclipse XDB-C18, 2.1×50 mm; solvent system: 5-95% (or 35-95%, or 65-95% or 95-95%) acetonitrile in water with 0.05% TFA; flow rate 0.8 mL/min; molecular weight range 500-1500; cone Voltage 20 V; column temperature 40° C.) or a Hewlett Packard System (Series 1100 HPLC; Column: Eclipse XDB-C18, 2.1×50 mm; solvent system: 1-95% acetonitrile in water with 0.05% TFA; flow rate 0.4 mL/min; molecular weight range 150-850; cone Voltage 50 V; column temperature 30° C.). All masses were reported as those of the protonated parent ions.

GCMS analysis is performed on a Hewlett Packard instrument (HP6890 Series gas chromatograph with a Mass Selective Detector 5973; injector volume: 1 μL; initial column temperature: 50° C.; final column temperature: 250° C.; ramp time: 20 minutes; gas flow rate: 1 mL/min; column: 5% phenyl methyl siloxane, Model No. HP 190915-443, dimensions: 30.0 m×25 m×0.25 m).

Nuclear magnetic resonance (NMR) analysis was performed on some of the compounds with a Varian 300 MHz NMR (Palo Alto, Calif.). The spectral reference was either TMS or the known chemical shift of the solvent. Some compound samples were run at elevated temperatures (e.g., 75° C.) to promote increased sample solubility.

The purity of some of the invention compounds is assessed by elemental analysis (Desert Analytics, Tucson, Ariz.).

Melting points are determined on a Laboratory Devices MeI-Temp apparatus (Holliston, Mass.).

Preparative separations were carried out using a Flash 40 chromatography system and KP-Sil, 60A (Biotage, Charlottesville, Va.), or by flash column chromatography using silica gel (230-400 mesh) packing material, or by HPLC using a C-18 reversed phase column. Typical solvents employed for the Flash 40 Biotage system and flash column chromatography were dichloromethane, methanol, ethyl acetate, hexane, acetone, aqueous hydroxyamine and triethyl amine. Typical solvents employed for the reverse phase HPLC were varying concentrations of acetonitrile and water with 0.1% trifluoroacetic acid.

Unless otherwise stated all temperatures are in degrees Celsius. Also, in these examples and elsewhere, abbreviations have the following meanings:

μg=micrograms
μl=microliter
μM=micromolar
aq=aqueous
DCM=dichloromethane
DIAD=diisopropyl diazodicarboxylate
DIEA=diisopropylethylamine
DMAP=dimethylaminopyridine
DMF=dimethylformamide
DMSO=dimethylsulfoxide
eq.=equivalence
g=gram
h=hour
HPLC=high performance liquid chromatography
kg=kilogram
L=liter
M=molar
mg=milligram
min=minute
ml=milliliter
mM=millimolar
mmol=millimole
mol=mole
N=normal
nm=nanometer
PTFE=teflon tetrafluoroethylene
rt=room temperature
THF=tetrahydrofuran Example 1

N-(3-aminopropyl)-N-[1-(3-benzylquinolin-2-yl)-2-methylpropyl]-3-fluoro-4-methylbenzamide (compound 1 in table 1)

Step 1. 3-benzyl-2-iodoquinoline

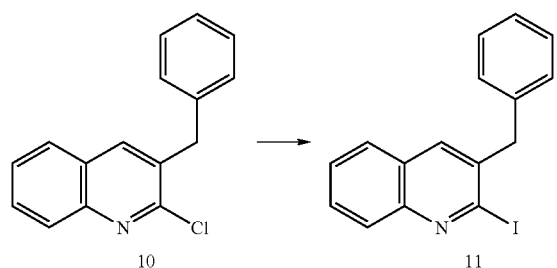

Quinoline 10 is prepared either by methods described herein or to conventional procedures known in the art. To a solution of quinoline 10 (1 eq., 5 g) and sodium iodide (10 eq., 29.5 g) in methyl ethyl ketone (40 ml), was added hydroiodic acid (excess, 20 ml). The reaction was refluxed at 80° C. for 8 h and then stirred at room temperature overnight. The solvent was evaporated and the residue was dissolved in ethyl acetate. The organic layer was washed with saturated sodium bicarbonate, saturated sodium chloride, sodium thiosulfate solution, dried over magnesium sulfate with charcoal, filtered through celite and concentrated. The brown oil was purified by flash chromatography to yield 7.5 g of the title product 11 as a greenish brown oil which was stored at 0° C.

Step 2.
1-(3-benzylquinolin-2-yl)-2-methylpropan-1-ol

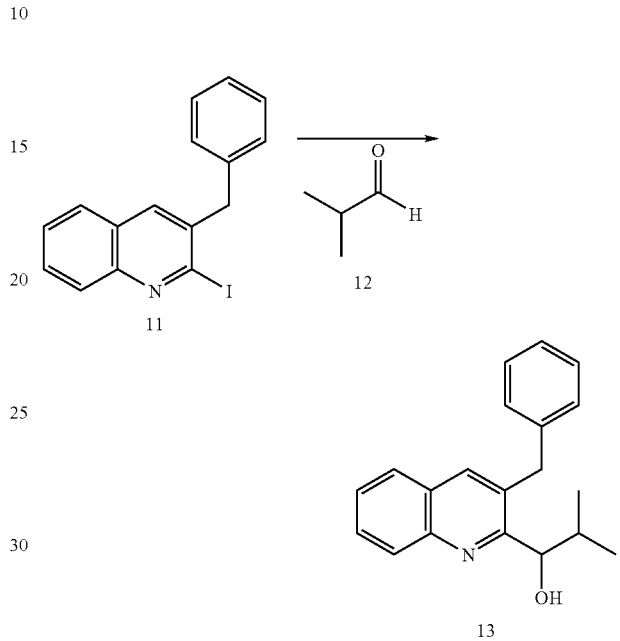

To a solution of 3-benzyl-2-iodoquinoline 11 (1 eq., 1.45 g) in dry tetrahydrofuran (20 ml) at −78° C., was added isopropyl magnesium chloride (3 eq., 6.3 ml). The color of the solution was changed from green to orange in 1 h. Isobutyraldehyde 12 (3 eq., 1.15 ml) was added and the reaction mixture was allowed to warm up to room temperature and stirred for another hour. Ethyl acetate was added. The organic layer was washed with saturated sodium bicarbonate, saturated sodium chloride, dried over magnesium sulfate, filtered and concentrated. The crude material was purified by flash chromatography to yield 150 mg of 1-(3-benzylquinolin-2-yl)-2-methylpropan-1-ol 13.

Step 3. 2-[1-(3-benzylquinolin-2-yl)-2-methylpropyl]-1H-isoindole-1,3(2H)-dione

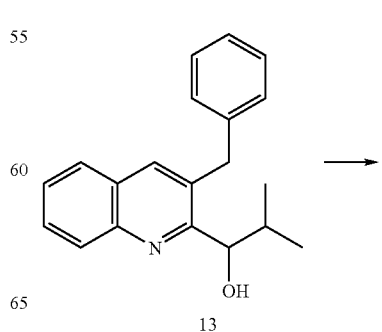

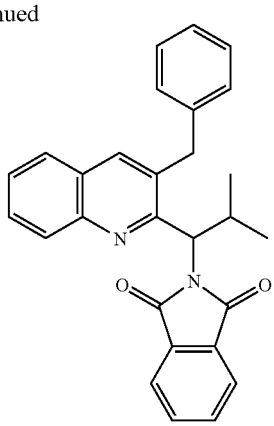

14

To a solution of 1-(3-benzylquinolin-2-yl)-2-methylpropan-1-ol 13 (102 mg, 1 eq.) in dry tetrahydrofuran (3 ml) at 0° C., was added phthalimide (154 mg, 3 eq), triphenylphosphine (138 mg, 1.5 eq.), and DIAD (1.5 eq., 104 μl). The reaction was allowed to warm to room temperature and stirred overnight. The solvent was evaporated. The residue was dissolved in ethyl acetate. The organic layer was washed with saturated sodium bicarbonate, saturated sodium chloride, dried over magnesium sulfate, filtered and concentrated. The material was purified by flash chromatography to yield 91 mg of 2-[1-(3-benzylquinolin-2-yl)-2-methylpropyl]-1H-isoindole-1,3(2H)-dione 14 as yellow oil.

Step 4.
1-(3-benzylquinolin-2-yl)-2-methylpropan-1-amine

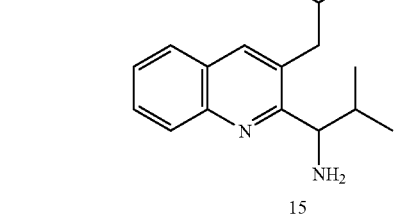

To a solution of 1-(3-benzylquinolin-2-yl)-2-methylpropan-1-amine 14 (91 mg, 1 eq.) in ethanol (2 ml), was added hydrazine (10 μl, 1.5 eq). The reaction was stirred at room temperature for an hour but very little product was detected. It was heated to 40° C. for 3 h and the 27% starting material was detected. More hydrazine (10 μl, 1.5 eq) was added and the reaction mixture was stirred for another half hour. The precipitate was filtered through a PTFE filter and washed with more CH$_2$Cl$_2$. The filtrate was concentrated and the crude product was purified by flash chromatography to yield 31 mg of 1-(3-benzylquinolin-2-yl)-2-methylpropan-1-amine 15 as clear oil.

Step 5. 2-(3-{[1-(3-benzylquinolin-2-yl)-2-methylpropyl]amino}propyl)-1H-isoindole-1,3(2H)-dione

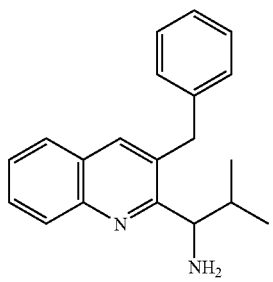

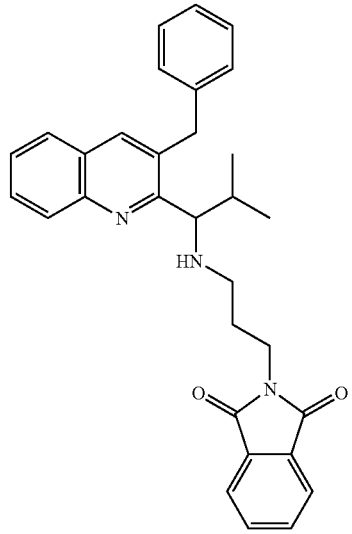

To a solution of 1-(3-benzylquinolin-2-yl)-2-methylpropan-1-amine 15 (31 mg, 1 eq.) in CH$_2$Cl$_2$ (3 ml), was added aldehyde 16 (0.8 eq., 17 mg), sodium triacetoxy borohydride, and acetic acid. The reaction mixture was stirred for 3 h at room temperature. Water was added and then the aqueous layer was extracted with ethyl acetate. The organic layer was washed with saturated sodium bicarbonate, saturated sodium chloride, dried over magnesium sulfate, filtered and concentrated to yield 46 mg of 2-(3-{[1-(3-benzylquinolin-2-yl)-2-methylpropyl]amino}propyl)-1H-isoindole-1,3(2H)-dione 17.

Step 6. N-[1-(3-benzylquinolin-2-yl)-2-methylpropyl]-3-fluoro-N-[3-(1,3-dioxo-1,3-dihydro-2H-isoindol-2-yl)propyl]-4-methylbenzamide to yield 19 mg of N-[1-(3-benzylquinolin-2-yl)-2-methylpropyl]-3-fluoro-N-[3-(1,3-dioxo-1,3-dihydro-2H-isoindol-2-yl)propyl]-4-methylbenzamide 19.

Step 7. N-(3-aminopropyl)-N-[1-(3-benzylquinolin-2-yl)-2-methylpropyl]-3-chloro-4-methylbenzamide

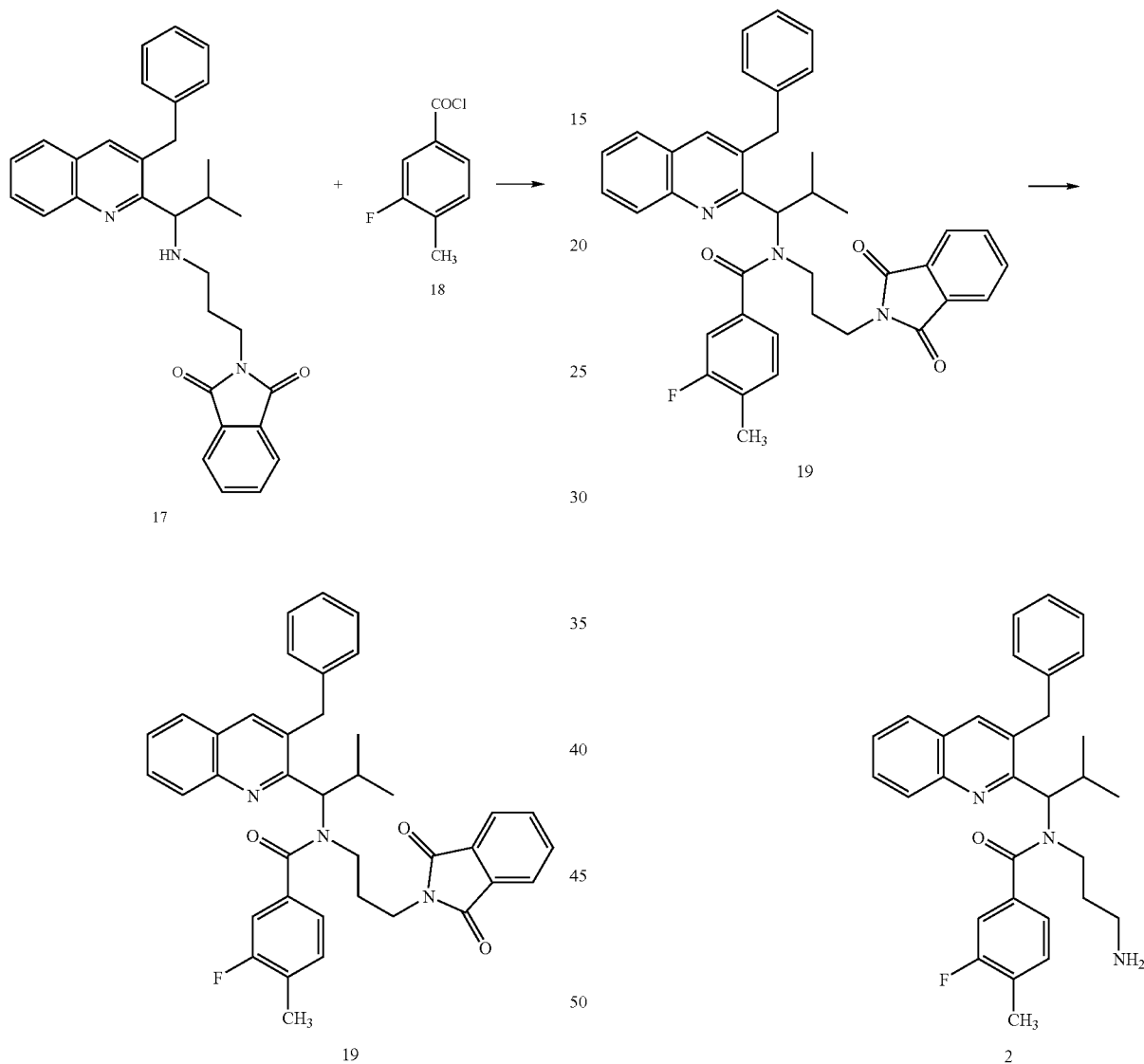

To a solution of 2-(3-{[1-(3-benzylquinolin-2-yl)-2-methylpropyl]amino}propyl)-1H-isoindole-1,3(2H)-dione 17 (15 mg, 1 eq.) in CH$_2$Cl$_2$ (1 ml), was added 3-fluoro-4-methyl benzoyl chloride 18 (11 mg, 2 eq.). Benzoyl chloride 18 is prepared using conventional means known in the art. Triethylamine (18 μl, 4 eq.) was then added. The reaction mixture was stirred at room temperature overnight. The reaction was quenched by adding water. The organic layer was washed with saturated sodium bicarbonate, saturated sodium chloride, dried over magnesium sulfate, filtered and concentrated To a solution of N-[1-(3-benzylquinolin-2-yl)-2-methylpropyl]-3-fluoro-N-[3-(1,3-dioxo-1,3-dihydro-2H-isoindol-2-yl)propyl]-4-methylbenzamide 19 (19 mg, 1 eq) in ethanol (1 ml), was added hydrazine (3 μl, 3 eq). The reaction was stirred at room temperature for 2 h then heated to 40° C. for another hour. The precipitate was filtered through a PTFE filter and washed with CH$_2$Cl$_2$. The filtrate was concentrated and purified by flash chromatography to yield 2 mg of N-(3-aminopropyl)-N-[1-(3-benzylquinolin-2-yl)-2-methylpropyl]-3-fluoro-4-methylbenzamide 2 as a white solid.

Example 2

N-(3-aminopropyl)-N-[1-(3-benzyl-7-chloroquinolin-2-yl)-2-methylpropyl]-4-Methylbenzamide (compound 4 in Table 1)

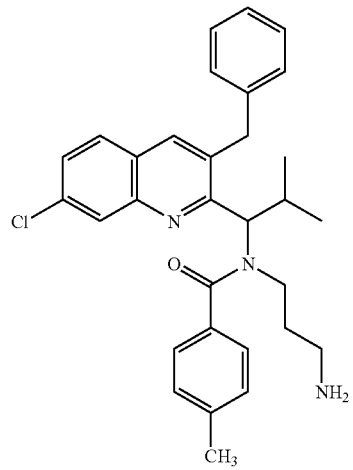

4

N-(3-Aminopropyl)-N-[1-(3-benzyl-7-chloroquinolin-2-yl)-2-methylpropyl]-4-methylbenzamide 4 was synthesized following steps and then employing similar procedures in steps 3-7 of example 1 starting with 1-(3-benzyl-7-chloroquinolin-2-yl)-2-methylpropan-1-ol in place of 1-(3-benzylquinolin-2-yl)-2-methylpropan-1-ol in step 3 of example 1.

Step 1. N-(3-chlorophenyl)-3-phenylpropanamide

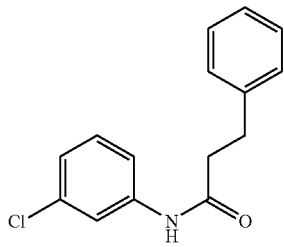

21

To a mixture of 3-chloroaniline (8.3 ml, 78.4 mmol), DMAP (1.0 g, 7.8 mmol), and pyridine (6.9 ml, 86.2 mmol) in anhydrous DCM (150 ml) at 0° C., was added 3-phenylpropionyl chloride (12.8 ml, 86.2 mmol). The mixture was warmed to ambient temperature and stirred under $N_2$ overnight. Excess DCM was added to the reaction mixture. The organic layer was washed with 1N HCl (3×), saturated $NaHCO_3$ (3×), brine, dried over $MgSO_4$, and the solvent was removed in vacuo to yield 21.6 g of N-(3-chlorophenyl)-3-phenylpropanamide 21 as a peach colored crude solid.

Step 2. 3-benzyl-2,7-dichloroquinoline

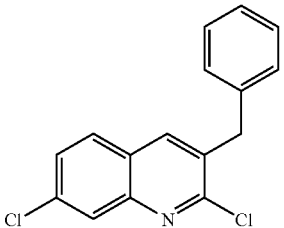

22

To $POCl_3$ (28.7 ml, 308 mmol) at 0° C., was added DMF (4.5 ml, 57.8 mmol) drop wise. The solution was stirred at 0° C. for one hour. N-(3-Chlorophenyl)-3-phenylpropanamide (10 g, 38.5 mmol) was added. The reaction mixture was allowed to warm to ambient temperature and then heated at 75° C. for 18 hours. The hot reaction mixture was poured onto 500 mL of ice and extracted with ethyl acetate (3×). The combined organic layers were washed with $NaHCO_3$, brine, dried over $MgSO_4$, filtered, and the solvent was removed in vacuo. The crude product was purified on ISCO purification system using ethyl acetate (0-100%) in hexane as eluting solvent to yield 8.1 g (28.1 mmol, 73%) 3-benzyl-2,7-dichloroquinoline 22 as a white solid.

Step 3. 3-benzyl-7-chloro-2 iodo-quinoline

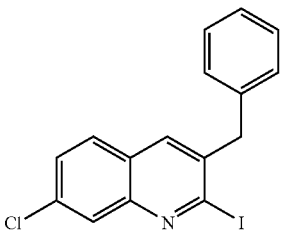

23

A mixture of 3-benzyl-2,7-dichloroquinoline (3.0 g, 10.4 mmol) and sodium iodide (15.6 g, 104 mmol) in 30 mL of methyl ethyl ketone was heated to 80° C. To this was added hydroiodic acid (1.13 ml, 13.2 mmol). The reaction mixture was heated at 80° C. for 1.5 hours and then cooled to ambient temperature. The reaction was quenched with $H_2O$. Excess ethyl acetate was added to the reaction mixture and the organic layer was washed with saturated $NaHCO_3$, saturated $Na_2S_2O_3$, brine, dried over $MgSO_4$, filtered and the solvent was removed in vacuo to yield 3.9 g (10.3 mmol, 99%) of 3-benzyl-7-chloro-2 iodo-quinoline 23 as a tan solid.

Step 4. 3-benzyl-7-chloroquinoline-2-carbaldehyde

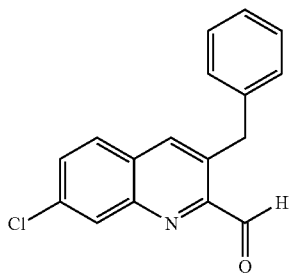

To a solution of 3-benzyl-7-chloro-2 iodo-quinoline (1.5 g, 3.95 mmol) in 15 mL of anhydrous THF at −78° C., was added isopropylmagnesium chloride (5.93 ml, 11.85 mmol). After stirring at −78° C. for 30 minutes, DMF (1.53 ml, 19.8 mmol) was added. The reaction mixture was allowed to slowly warm to ambient temperature over two hours. It was then quenched with saturated NH$_4$Cl and extracted with ethyl acetate (3×). The combined organic layers were washed with brine, dried over MgSO$_4$, and the solvent was removed in vacuo yielding 1.23 g of 3-benzyl-7-chloroquinoline-2-carbaldehyde 24 as brown oil.

Step 5. 1-(3-benzyl-7-chloroquinolin-2-yl)-2-methyl-propan-1-ol

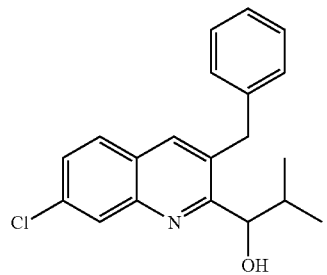

To a solution of 3-benzyl-7-chloroquinoline-2-carbaldehyde (1.23 g, 4.4 mmol) in anhydrous DCM (12 ml) at −78° C., was added isopropylmagnesium chloride (6.6 m, 13.2 mmol). The resulting solution was allowed to warm to ambient temperature over one hour. The reaction mixture was then quenched with saturated NH$_4$Cl and extracted with DCM (3×). The combined organic layers were washed with brine, dried over MgSO$_4$, and the solvent was removed in vacuo. The crude product was subjected to flash column chromatography using an ISCO purification system. Elution in hexanes with a gradient of ethyl acetate (0-100%) yielded 1-(3-benzyl-7-chloroquinolin-2-yl)-2-methylpropan-1-ol 25 (0.44 g, 1.3 mmol, 30%) as a red oil.

The compounds in the table below may be prepared using the methodology described in the previous Examples and Methods. The starting materials used in the synthesis are recognizable to one of skill in the art and are commercially available or may be prepared using known methods. The compounds were named using ACD/Name Batch Version 5.04 (Advanced Chemistry Development Inc.; Toronto, Ontario; www.acdlabs.com).

| Compound | Structure | MH+ | Name |
|---|---|---|---|
| 1 | 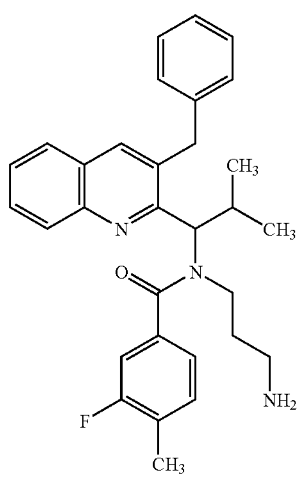 | 484.2 | N-(3-aminopropyl)-N-[1-(3-benzylquinolin-2-yl)-2-methylpropyl]-3-fluoro-4-methylbenzamide |

-continued

| Compound | Structure | MH+ | Name |
|---|---|---|---|
| 2 | 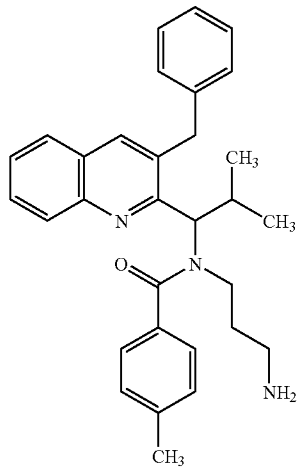 | 466.2 | N-(3-aminopropyl)-N-[1-(3-benzylquinolin-2-yl)-2-methylpropyl]-4-methylbenzamide |
| 3 | 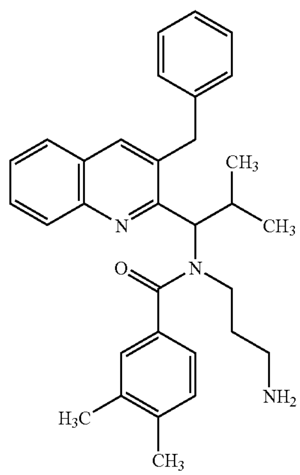 | 480.2 | N-(3-aminopropyl)-N-[1-(3-benzylquinolin-2-yl)-2-methylpropyl]-3,4-dimethylbenzamide |
| 4 | 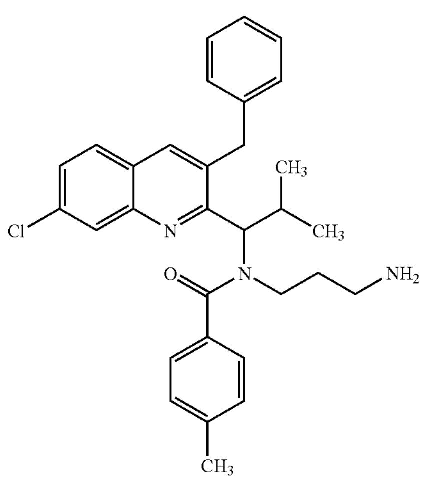 | 500.2 | N-(3-aminopropyl)-N-[1-(3-benzyl-7-chloroquinolin-2-yl)-2-methylpropyl]-4-methylbenzamide |

| Compound | Structure | MH+ | Name |
|---|---|---|---|
| 5 | 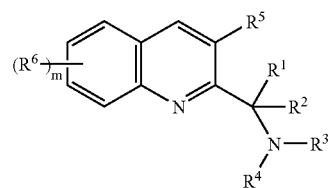 | 518.2 | N-(3-aminopropyl)-N-[1-(3-benzyl-7-chloroquinolin-2-yl)-2-methylpropyl]-3-fluoro-4-methylbenzamide |

Example 3

Assay for Determining KSP Activity

This example provides a representative in vitro assay for determining ivity in vitro. Purified microtubules obtained from bovine brain were purchased from Cytoskeleton Inc. (Denver, Colo., USA). The motor domain of human KSP (Eg 5, KNSL1) was cloned, expressed, and purified to greater than 95% homogeneity. Biomol Green was purchased from Affinity Research Products Ltd. (Matford Court, Exeter, Devon, United Kingdom). Microtubules and KSP motor protein (i.e., the KSP motor domain) were diluted in assay buffer (20 mM Tris-HCl (pH 7.5), 1 mM $MgCl_2$, 10 mM DTT and 0.25 mg/ml BSA) to a final concentration of 35 μg/ml microtubules and 45 nM KSP. The microtubule/KSP mixture was then pre-incubated at 37° C. for 10 min to promote the binding of KSP to microtubules.

To each well of the testing plate (384-well plate) containing 1.25 μl of inhibitor or test compound in DMSO (or DMSO only in the case of controls) were added 25 μl of ATP solution (ATP diluted to a concentration of 300 μM in assay buffer) and 25 μl of the above-described microtubule/KSP solution. The plates were incubated at room temperature for 1 hour. Following incubation, 65 μl of Biomol Green (a malachite green-based dye that detects the release of inorganic phosphate) was added to each well. The plates were incubated for an additional 5-10 minutes then the absorbance at 630 nm was determined using a Victor II plate reader. The amount of absorbance at 630 nm corresponded to the amount of KSP activity in the samples. The $IC_{50}$ of each inhibitor or test compound was then determined based on the decrease in absorbance at 630 nm at each concentration, via nonlinear regression using either XLFit for Excel or Prism data analysis software by GraphPad Software Inc.

Preferred compounds of the invention have a biological activity as measured by an $IC_{50}$ per Example 3 below of less than about 1 mM, with preferred embodiments having biological activity of less than about 25 μM, with particularly preferred embodiments having biological activity of less than about 1000 nM, and with the most preferred embodiments having biological activity of less than about 100 nM.

What is claimed is:

1. A compound of formula I:

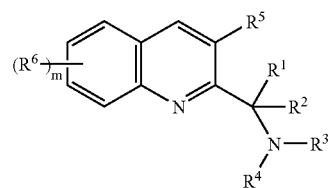

wherein:

m is an integer from 0 to 3;

$R^1$ is selected from the group consisting of acylamino, carboxyl ester, and $C_1$ to $C_5$ alkyl optionally substituted with hydroxy, or halo;

$R^2$ is hydrogen or $C_1$ to $C_5$ alkyl;

$R^3$ is —C(=X)-A, wherein A is selected from the group consisting of aryl, heteroaryl, heterocyclic, and cycloalkyl, all of which may be optionally substituted with 1 to 4 substituents selected from the group consisting of $C_1$ to $C_4$ alkyl, $C_1$ to $C_4$ alkoxy, halo, hydroxy, and nitro and X is oxygen or sulfur;

$R^4$ is -alkylene-heterocyclic or -alkylene-$NR^7R^8$ wherein alkylene is a $C_1$ to $C_4$ straight chained alkylene; $R^7$ and $R^8$ are independently selected from the group consisting of hydrogen, $C_1$ to $C_4$ alkyl, arylalkyl, heteroarylalkyl, cycloalkyl and cycloalkylalkyl;

$R^5$ is selected from the group consisting of L-$A^1$, wherein $A^1$ is selected from the group consisting of aryl, heteroaryl, heterocyclic, and cycloalkyl, all of which may be optionally substituted with 1 to 4 substituents selected from the group consisting of $C_1$ to $C_4$ alkyl, $C_1$ to $C_4$ alkoxy, halo, hydroxy, and nitro and wherein L is selected from the group consisting of oxygen, —$NR^9$ where $R^9$ is hydrogen or alkyl, —$S(O)_q$— where q is zero, one or two, and $C_1$ to $C_5$ alkylene, optionally substituted with hydroxy, halo, or acylamino; and $R^6$ is selected from the group consisting of $C_1$ to $C_5$ alkyl, $C_2$ to $C_5$ alkenyl, $C_2$ to $C_5$ alkynyl, —$CF_3$, $C_1$ to $C_5$ alkoxy, halo, and hydroxy;

or a pharmaceutically acceptable salt thereof.

2. The compound of claim 1, wherein the compound is represented by formula II:

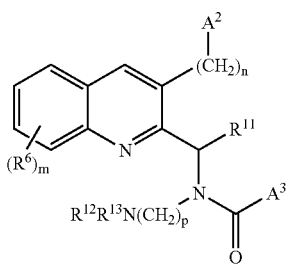

wherein:
  $A^2$ and $A^3$ are independently selected from the group consisting of aryl, heteroaryl, heterocyclic, and cycloalkyl, all of which may be optionally substituted with 1 to 4 substituents selected from the group consisting of $C_1$ to $C_4$ alkyl, $C_1$ to $C_4$ alkoxy, halo, hydroxy, and nitro;
  each $R^6$ is independently selected from the group consisting of $C_1$ to $C_5$ alkyl, $C_2$ to $C_5$ alkenyl, $C_2$ to $C_5$ alkynyl, -$CF_3$, $C_1$ to $C_5$ alkoxy, halo and hydroxyl;
  $R^{11}$ is $C_2$ to $C_3$ alkyl;
  $R^{12}$ and $R^{13}$ are independently selected from the group consisting of hydrogen, $C_1$ to $C_4$ alkyl, arylalkyl, heteroarylalkyl, cycloalkyl and cycloalkylalkyl;
  m is an integer equal to 0 to 2;
  n is an integer equal to 1 to 3; and
  p is an integer equal to 1 to 4;
or a pharmaceutically acceptable salt thereof.

3. The compound of claim 1, wherein the compound is represented by formula III:

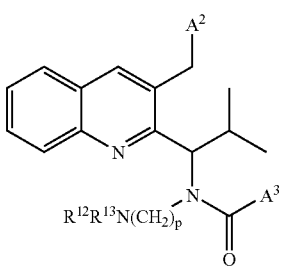

wherein:
  $A^2$ and $A^3$ are independently selected from the group consisting of aryl, heteroaryl, heterocyclic, and cycloalkyl, all of which may be optionally substituted with 1 to 4 substituents selected from the group consisting of $C_1$ to $C_4$ alkyl, $C_1$ to $C_4$ alkoxy, halo, hydroxy, and nitro;
  $R^{12}$ and $R^{13}$ are independently selected from the group consisting of hydrogen, $C_1$ to $C_4$ alkyl, arylalkyl, heteroarylalkyl, cycloalkyl and cycloalkylalkyl;
  p is an integer equal to 1 to 4;
or a pharmaceutically acceptable salt thereof.

4. The compound of claim 1, wherein $R^1$ is $C_1$ to $C_5$ alkyl.

5. The compound of claim 1, wherein $R^1$ is isopropyl or t-butyl.

6. The compound of claim 1, wherein $R^2$ is hydrogen or methyl.

7. The compound of claim 1, wherein X is oxygen.

8. The compound of claim 1, wherein A is aryl.

9. The compound of claim 1, wherein A is phenyl or naphthyl.

10. The compound of claim 1, wherein A is heteroaryl.

11. The compound of claim 1, wherein A is selected from the group consisting of pyridinyl, imidazolyl, furanyl, pyrazolyl, and thiazolyl.

12. The compound of claim 1, wherein A is cycloalkyl.

13. The compound of claim 1, wherein A is cyclohexyl.

14. The compound of claim 1, wherein A is substituted with 1 to 4 substituents selected from the group consisting of chloro, methyl, bromo, fluoro, nitro, -$CF_3$, methoxy, and t-butyl.

15. The compound of claim 1, wherein —C(O)-A is selected from the group consisting of:
  (2-chloro-6-methylpyridin-4-yl)carbonyl;
  (5-methylimidazol-4-yl)carbonyl;
  (naphth-2-yl)carbonyl;
  (pyridin-3-yl)carbonyl;
  (pyridin-4-yl) carbonyl;
  3,4-difluorobenzoyl;
  3,4-dimethylbenzoyl;
  3,5-dimethylpyrazol-3-ylcarbonyl;
  2-(3-aminopropanamido)- 4-methylbenzoyl;
  2,4-difluorobenzoyl;
  2,6-difluorobenzoyl;
  2-chlorobenzoyl;
  2-chloropyridin-3-ylcarbonyl;
  2-chloropyridin-5-ylcarbonyl;
  2-fluorobenzoyl;
  2-methoxybenzoyl;
  3,4-dichlorobenzoyl;
  3-chlorobenzoyl;
  3-fluoro-4-methylbenzoyl;
  4-bromobenzoyl;
  4-chlorobenzoyl;
  4-hydroxybenzoyl;
  4-methoxybenzoyl;
  4-methyl-3-fluorobenzoyl;
  4-methylbenzoyl;
  4-nitrobenzoyl;
  4-t-butylbenzoyl;
  4-trifluoromethylbenzoyl;
  benzoyl;
  cyclohexylcarbonyl;
  furan-3 -ylcarbonyl;
  pyridin-2-ylcarbonyl; and
  thiazol-4-ylcarbonyl.

16. The compound of claim 15, wherein —C(O)-A is selected from the group consisting of 4-methyl-3-fluorobenzoyl, 4-methylbenzoyl, and 3,4-dimethylbenzoyl.

17. The compound of claim 1, wherein $R^4$ is selected from the group consisting of:
  3-(benzylamino) propyl;
  3-(cyclobutylamino) propyl;
  3-(cyclohexylmethylamino) propyl;
  3-(diethylamino)propyl;
  3-(isopropylamino) propyl;
  3- [(3 -trifluoromethylpyridin-6-yl)amino]propyl;
  3 -aminopropyl;
  2-aminoethyl;
  piperidin-3-ylmethyl; and
  pyrrolidin-3 -ylmethyl.

18. The compound of claim 1, wherein $R^4$ is 3-aminopropyl.

19. The compound of claim 1, wherein $R^5$ is alkylene-$A^1$ and $A^1$ is aryl.

20. The compound of claim 19, wherein $R^5$ is selected from the group consisting of:
   benzyl;
   2-methylbenzyl;
   3,5-difluorobenzyl;
   3-acetylaminobenzyl;
   3-fluorobenzyl;
   3-hydroxybenzyl;
   4-chlorobenzyl;
   4-difluorobenzyl; and
   4-methylbenzyl.

21. The compound of claim 1, wherein $R^6$ is selected from the group consisting of hydrogen, fluoro, chloro, methyl, bromo, ethyl, vinyl, methoxy, phenyl, ethynyl, and —$CF_3$.

22. The compound of claim 2, wherein m is 1 and n is 1.

23. The compound of claim 2, wherein $R^{11}$ is isopropyl.

24. The compound of claim 2, wherein p is 3.

25. The compound of claim 2, wherein $R^{12}$ and $R^{13}$ are hydrogen.

26. The compound of claim 2, wherein $A^2$ is phenyl.

27. The compound of claim 3, wherein $A^2$ is phenyl.

28. The compound of claim 3, wherein p is 3.

29. The compound of claim 3, wherein $R^{12}$ and $R^{13}$ are hydrogen.

30. A compound selected from the group consisting of:
   N-(3-aminopropyl)-N- [1-(3-benzylquinolin-2-yl)- 2-methylpropyl]-3-fluoro-4-methylbenzamide;
   N-(3-aminopropyl)-N-[1-(3-benzylquinolin-2-yl)-2-methylpropyl]-4-methylbenzamide;
   N-(3-aminopropyl)-N-[1-(3-benzylquinolin-2-yl)-2-methylpropyl]-3,4-dimethylbenzamide;
   N-(3-aminopropyl)-N-[1-(3-benzyl-7-chloroquinolin-2-yl)- 2-methylpropyl]-4-methylbenzamide;
   N-(3-aminopropyl)-N-[1-(3-benzyl-7-chloroquinolin-2-yl)- 2-methylpropyl]-3-fluoro-4-methylbenzamide; and
   a pharmaceutically acceptable salt thereof.

31. A pharmaceutical composition comprising a therapeutically effective amount of a compound of claim 1 and a pharmaceutically acceptable carrier.

32. The composition of claim 31 further comprising at least one additional agent for the treatment of cancer.

33. The composition of claim 31, wherein the additional agent for the treatment of cancer is selected from the group consisting of irinotecan, topotecan, gemcitabine, imatinib, trastuzumab, 5-fluorouracil, leucovorin, carboplatin, cisplatin, docetaxel, paclitaxel, tezacitabine, cyclophosphamide, vinca alkaloids, anthracyclines, rituximab, and trastuzumab.

* * * * *

UNITED STATES PATENT AND TRADEMARK OFFICE
CERTIFICATE OF CORRECTION

PATENT NO. : 7,452,996 B2
APPLICATION NO. : 11/133509
DATED : November 18, 2008
INVENTOR(S) : Wang et al.

It is certified that error appears in the above-identified patent and that said Letters Patent is hereby corrected as shown below:

On the Title Page

Item [*] Notice: Subject to any disclaimer, the term of this patent is extended or adjusted under 35 U.S.C. 154(b) by (611) days Delete the phrase "by 611 days" and insert -- by 794 days --

Signed and Sealed this

First Day of June, 2010

David J. Kappos
*Director of the United States Patent and Trademark Office*